(12) United States Patent
Muratsubaki et al.

(10) Patent No.: US 8,021,766 B2
(45) Date of Patent: Sep. 20, 2011

(54) BENZO(GHI)FLUORANTHENE DERIVATIVE AND ORGANIC LIGHT EMITTING DEVICE USING THE SAME

(75) Inventors: Masanori Muratsubaki, Hachioji (JP); Akihito Saitoh, Yokohama (JP); Satoshi Igawa, Fujisawa (JP); Takao Takiguchi, Chofu (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 464 days.

(21) Appl. No.: 12/118,227

(22) Filed: May 9, 2008

(65) Prior Publication Data

US 2008/0286611 A1 Nov. 20, 2008

(30) Foreign Application Priority Data

May 14, 2007 (JP) .................................. 2007-127794

(51) Int. Cl.
*H01L 51/54* (2006.01)
*C07C 211/43* (2006.01)
*C07C 13/48* (2006.01)

(52) U.S. Cl. ........ 428/690; 428/917; 313/504; 313/506; 564/427; 585/26

(58) Field of Classification Search .................. None
See application file for complete search history.

(56) References Cited

U.S. PATENT DOCUMENTS

| 7,338,721 | B2 | 3/2008 | Suzuki et al. ............... 428/690 |
| 2004/0076853 | A1 | 4/2004 | Jarikov .......................... 428/690 |
| 2006/0097227 | A1 | 5/2006 | Okajima et al. ......... 252/301.16 |
| 2007/0249878 | A1 | 10/2007 | Iwawaki et al. .............. 585/27 |
| 2007/0252141 | A1 | 11/2007 | Negishi et al. ............... 257/40 |
| 2007/0273272 | A1* | 11/2007 | Kubota ........................ 313/504 |
| 2008/0124577 | A1 | 5/2008 | Saitoh et al. ................. 428/704 |

FOREIGN PATENT DOCUMENTS

| JP | 10/189247 | 7/1998 |
| JP | 2005-068087 | 3/2005 |
| JP | 2005-272805 | 10/2005 |

OTHER PUBLICATIONS

Peng et al., Journal of the American Chemical Society, (2005), vol. 127 (47), pp. 16518-16521.*

Wang et al., Tetrahedron Letters, (2000), vol. 41 (3), pp. 285-288.*
Barder et al., "Catalysts for Suzuki—Miyaura Coupling Processes: Scope and Studies of the Effect of Ligand Structure," *J. Am. Chem. Soc.*, vol. 127, 4685-4696 (2005).
Liu et al., "Improved Methodology for Photocyclization Reactions," *American Chemical Society* vol. 56, 3769-3775 (1991).
Tang et al., "Organic Electroluminescent Diodes," *Appl. Phys. Lett. 51*, 913-915 (1987).
Bonnet et al., "Efficient Hydrodehalogenation of Halo Aromatic Compounds on Sulfided $CoO/MoO_3/Al_2O_3/$ and $Nio/MoO_3/Al_2O_3$ Catalysts," *J. Org. Chem.*; vol. 48 4396-4397 (1983).

* cited by examiner

*Primary Examiner* — Dawn L. Garrett
(74) *Attorney, Agent, or Firm* — Fitzpatrick, Cella, Harper & Scinto

(57) ABSTRACT

To provide an organic light emitting device with high color purity, high efficiency, high luminance, and a long life, the organic light emitting device includes: a pair of electrodes having an anode and a cathode, and at least one layer containing an organic compound sandwiched between the pair of electrodes, at least one of the anode and the cathode being transparent or translucent, in which at least one layer containing an organic compound contains at least one kind of the benzo(ghi)fluoranthene derivative represented by the following General Formula (1) or (2).

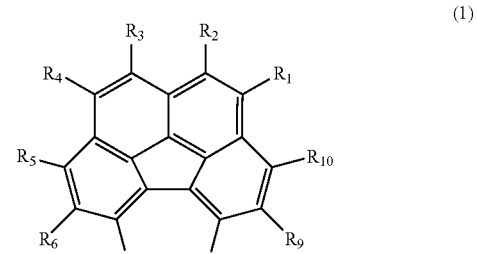

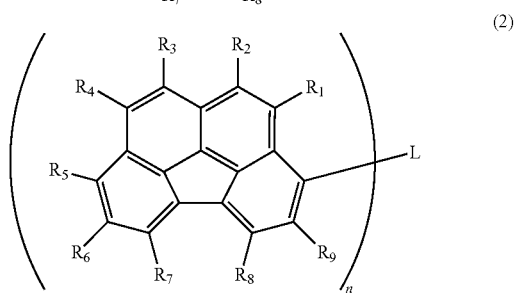

5 Claims, 3 Drawing Sheets

BENZO(GHI)FLUORANTHENE DERIVATIVE AND ORGANIC LIGHT EMITTING DEVICE USING THE SAME

BACKGROUND OF THE INVENTION

1. Field of the Invention

The present invention relates to an organic light emitting device, and more specifically to an organic light emitting device using a benzofluoranthene derivative.

2. Description of the Related Art

An organic light emitting device is a device in which a thin film including a fluorescent organic compound or a phosphorescent organic compound is sandwiched between an anode and a cathode. Further, electrons and holes are injected from the respective electrodes to generate exciton of the fluorescent compound, whereby the organic light emitting device emits light when the exciton returns to a ground state.

According to a study at Eastman Kodak company in 1987 (Appl. Phys. Lett. 51, 913 (1987)), there is reported a device having a function-separation type two-layer structure. Specifically, there is reported a device using ITO as an anode, a magnesium-silver alloy as a cathode, an aluminum quinolinol complex as an electron transporting material and a light emitting material, and a triphenylamine derivative as a hole transporting material. In the device having the function-separation type two-layer structure, there is reported a light emission of approximately 1,000 cd/m$^2$ at an applied voltage of approximately 10 V.

Recent progress of an organic light emitting device is remarkable, and the characteristics of the device enable a light emitting device with a high luminance at a low applied voltage, a variety of emission wavelengths, high-speed responsiveness, thin and light weight. From this fact, it is suggested that the organic light emitting device have potential to find use in a wide variety of applications. The organic light emitting device still involves many problems in terms of durability such as a change with time due to long-term use and deterioration due to, for example, an atmospheric gas containing oxygen or humidity. Further, when it is attempted that the device is applied to a full-color display, at present, blue light, green light, and red light each having a longer life, high conversion efficiency, and high color purity need to emitted. Various proposals have been made so as to solve the problems.

Here, in order to solve the problems, a benzofluoranthene derivative has been proposed as a material for the organic light emitting device. Japanese Patent Application Laid-Open No. H10-189247, Japanese Patent Application Laid-Open No. 2005-68087, and Japanese Patent Application Laid-Open No. 2005-272805 report an organic light emitting device using a benzo(k)fluoranthene derivative. Moreover, US Patent Application Publication No. 2004-0076853 reports that an unsubstituted benzo(ghi)fluoranthene is not suitable as a light emitting material due to large intermolecular interaction and that an unsubstituted indeno chrysene is used as a second host material that is likely to form an aggregate. Moreover, US Patent Application Publication No. 2004-0076853 reports an example in which a benzo(ghi)fluoranthene, in which an unsubstituted benzene ring has been introduced to the 1st and 6th positions, has been used similarly as a second host material that is likely to form an aggregate.

SUMMARY OF THE INVENTION

The present invention was made so as to solve the above-described problems of the conventional techniques. The present invention aims to provide a compound having a high efficiency, high luminance, and long life for an organic light emitting device and an organic light emitting device using such a compound. The present invention also aims to provide an organic light emitting device, which can be produced readily and at a relatively low cost.

The benzo(ghi)fluoranthene derivative of the present invention is represented by General Formula (1) or (2).

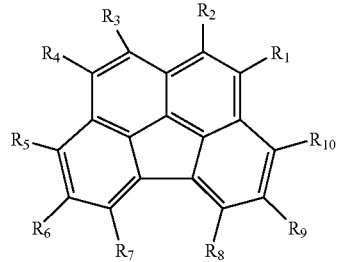

(1)

wherein $R_1$ to $R_{10}$ each independently represent a substituent selected from a hydrogen atom, a $C_{2-20}$ alkyl group, a substituted or unsubstituted alkenyl group, a substituted or unsubstituted alkynyl group, a silyl group, a substituted or unsubstituted aryl group having two or more rings, and a substituted or unsubstituted fused polycyclic heterocyclic group; $R_1$ to $R_{10}$ each may be the same or different; and at least one of $R_1$ to $R_{10}$ represents a group selected from a $C_{2-20}$ alkyl group, a substituted or unsubstituted aryl group having two or more rings, and a substituted or unsubstituted fused polycyclic heterocyclic group.

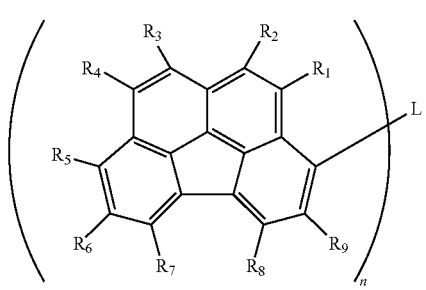

(2)

wherein n represents an integer of 2 to 4; L represents a single bond or divalent to tetravalent connecting groups derived from any one of a substituted or unsubstituted alkane, a substituted or unsubstituted alkene, alkyne, and a substituted or unsubstituted aromatic ring; $R_1$ to $R_9$ each independently represent a substituent selected from a hydrogen atom, a $C_{2-20}$ alkyl group, a substituted or unsubstituted alkenyl group, a substituted or unsubstituted alkynyl group, a silyl group, a substituted amino group, a substituted or unsubstituted aryl group having two or more rings, and a substituted or unsubstituted fused polycyclic heterocyclic group; and $R_1$ to $R_9$ each may be the same or different.

The present invention can provide a compound having a high efficiency, high luminance, and long life for an organic light emitting device and an organic light emitting device using such a compound. The present invention also can provide an organic light emitting device, which can be produced readily and at a relatively low cost.

Further features of the present invention will become apparent from the following description of exemplary embodiments with reference to the attached drawings.

DESCRIPTION OF THE EMBODIMENTS

Figure 1:
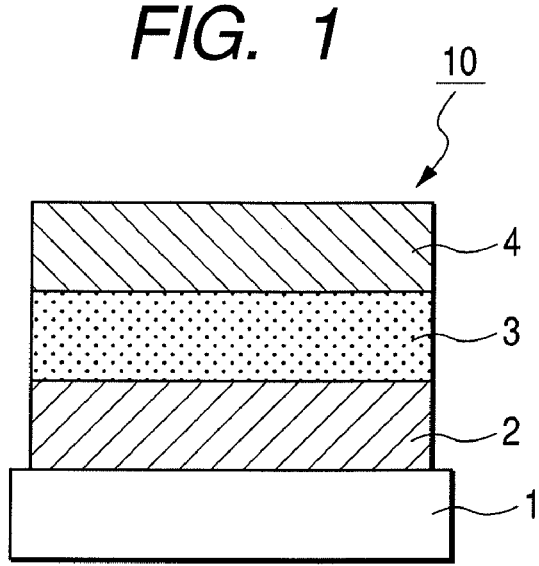
FIG. 1 is a cross sectional view illustrating an organic light emitting device according to a first embodiment of the present invention.

Hereinafter, the present invention will be described in detail.

First, a benzo(ghi)fluoranthene derivative of the present invention will be described in detail.

The benzo(ghi)fluoranthene derivative of the present invention is represented by General Formula (1).

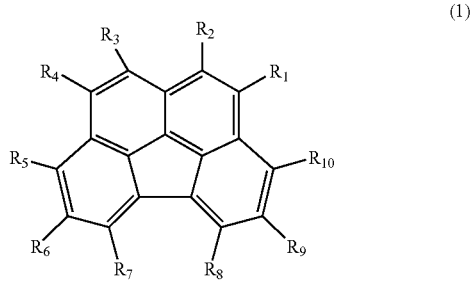

(1)

In General Formula (1), $R_1$ to $R_{10}$ each independently represent a substituent selected from a hydrogen atom, a $C_{2-20}$ alkyl group, an aralkyl group, a substituted or unsubstituted alkenyl group, a substituted or unsubstituted alkynyl group, a silyl group, a substituted amino group, a substituted or unsubstituted aryl group having two or more rings, and a substituted or unsubstituted fused polycyclic heterocyclic group.

In General Formula (1), it is preferred that one of $R_5$ and $R_{10}$ be a substituent selected from a substituted or unsubstituted aryl group having two or more rings and a substituted or unsubstituted fused polycyclic heterocyclic group. In this case, $R_5$ and $R_{10}$ each may be the same or different.

Examples of an alkyl group having 2 to 20 carbon atoms represented by $R_1$ to $R_{10}$ include, but are of course not limited to, an ethyl group, an ethyl-d5 group, an n-propyl group, an n-butyl group, an n-pentyl group, an n-hexyl group, an n-heptyl group, an n-octyl group, an n-decyl group, an iso-propyl group, an iso-propyl-d7 group, an iso-butyl group, a sec-butyl group, a tert-butyl group, a tert-butyl-d9 group, an iso-pentyl group, a neopentyl group, a tert-octyl group, a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a 5-fluoropentyl group, a 6-fluorohexyl group, a chloromethyl group, a trichloromethyl group, 2-chloroethyl group, a 2,2,2-trichloroethyl group, a 4-chlorobutyl group, a 5-chloropentyl group, a 6-chlorohexyl group, a bromomethyl group, a 2-bromoethyl group, an iodomethyl group, a 2-iodethyl group, a hydroxymethyl group, a hydroxyethyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a norbornyl group, an adamantyl group, a benzyl group, a 2-phenylethyl group, a 2-phenylisopropyl group, a 1-naphthylmethyl group, a 2-naphthylmethyl group, a 2-(1-naphthyl)ethyl group, a 2-(2-naphthyl)ethyl group, a 9-anthrylmethyl group, a 2-(9-anthryl)ethyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, and a 4-bromobenzyl group.

Examples of an alkenyl group represented by $R_1$ to $R_{10}$ include, but are of course not limited to, a vinyl group, a 1-propenyl group, a 2-propenyl group, a 1-butenyl group, a 2-butenyl group, and a 3-butenyl group.

As the alkynyl group represented by $R_1$ to $R_{10}$, an ethynyl group, a 1-propynyl group, a 2-propynyl group, a 1-butynyl group, a 2-butynyl group, and a 3-butynyl group are mentioned. Examples of the alkynyl group represented by $R_1$ to $R_{10}$ are not limited to the above.

As the silyl group represented by $R_1$ to $R_{10}$, a trimethylsilyl group, a triethylsilyl group, and a triisopropylsilyl group are mentioned. Examples of the silyl group represented by $R_1$ to $R_{10}$ are not limited to the above.

As the aryl group represented by $R_1$ to $R_{10}$ having two or more rings refer to the following substituents.

(1) Substituent in which a plurality of benzene rings is bonded to each other at arbitrary positions (2) Fused polycyclic aromatic group (3) Substituent in which one or more benzene rings are bonded to a fused polycyclic aromatic ring at suitable positions Examples of the substituent in the item (1) include a biphenyl group and a terphenyl group.

Specific examples of the group in the item (2) include, of course not limited to, a naphthyl group, a naphthyl-d7 group, an acenaphthylenyl group, an anthryl group, an anthryl-d9 group, a phenanthryl group, a phenanthryl-d9 group, a pyrenyl group, a pyrenyl-d9 group, an acephenanthrylenyl group, an aceanthrylenyl group, a chrysenyl group, a dibenzochrysenyl group, a benzoanthryl group, a benzoanthryl-d11 group, a dibenzoanthryl group, a naphthacenyl group, a picenyl group, a pentacenyl group, a fluorenyl group, a triphenylenyl group, a pyrenyl group, pyrenyl-d-11, a fluoranthenyl group, and a benzo[k]fluoranthenyl group.

The substituent (3) above specifically refers to a substituent in which a benzene ring or the substituent mentioned in (1) above is bonded to a fused polycyclic aromatic group mentioned as a specific example of the fused polycyclic aromatic group above (2).

Examples of the condensed hetelocyclic group represented by $R_1$ to $R_{10}$ include, of course not limited to, a benzothienyl group, a dibenzothienyl group, a dibenzothienyl-d7 group, a benzofuryl group, an isobenzofuryl group, a dibenzofuryl group, a dibenzofuryl-d7 group, a quinolyl group, a quinolyl-d6 group, an isoquinolyl group, a quinoxalinyl group, a naphthridinyl group, a quinazolinyl group, a phenantridinyl group, an indolidinyl group, a phenadinyl group, a carbazolyl group, an acridinyl group, an azafluorenyl group, an azafluoranthenyl group, and an azabenzofluoranthenyl group.

Examples of the substituent that the alkenyl group, alkynyl group, aryl group, and condensed polyheterocyclic group may further contain include, of course not limited to: alkyl groups such as a methyl group, an ethyl group, a propyl group, and a tert-butyl group; aryl groups such as a phenyl group, a biphenyl group, a fluorenyl group, and a bifluorenyl group; heterocyclic groups such as a thienyl group, a pyrrolyl group, and a pyridyl group; substituted amino groups such as a dimethylamino group, a diethylamino group, a dibenzylamino group, a diphenylamino group, a ditolylamino group, and a dianisolylamino group; halogen atoms such as fluorine, chlorine, bromine, and iodine.

$R_1$ to $R_{10}$ each may be the same or different. It should be noted that at least one of $R_1$ to $R_{10}$ represents a group selected from a $C_{2\text{-}20}$ alkyl group, a substituted or unsubstituted aryl group having two or more rings, and a substituted or unsubstituted fused polycyclic heterocyclic group.

As another embodiment of the benzo(ghi)fluoranthene derivative of the present invention, a compound represented by General Formula (2) is mentioned.

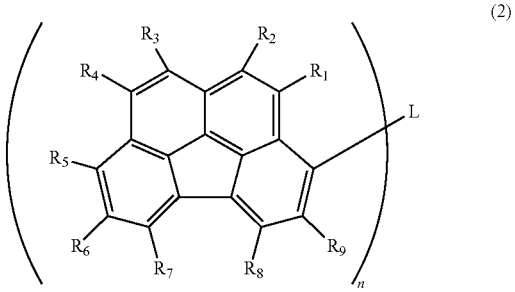

(2)

wherein, n represents an integer of 2 to 4.

L represents a single bond or divalent to tetravalent connecting groups derived from any one of a substituted or unsubstituted alkane, a substituted or unsubstituted alkene, alkyne, and a substituted or unsubstituted aromatic ring.

As the connecting group, which is represented by L and derived from alkane, an ethylene group, a propylene group, a butylene group, etc., are mentioned. The examples of the connecting group are not limited to the above.

As the connecting group, which is represented by L and derived from alkane, an ethylene group, a propylene group, a butylene group, etc., are mentioned. The examples of the connecting group are not limited to the above.

As the connecting group, which is represented by L and derived from alkane, an ethylene group, a propylene group, a butylene group, etc., are mentioned. The examples of the connecting group are not limited to the above.

As the connecting group which is represented by L and derived from an aromatic ring, a phenylene group, a biphenylene group, a fluolenylene group, a naphthylene group, an anthrylene group, a crycenylene group, divalent to tetravalent substituents derived from 5-phenyl-1,1':3',1'''-terphenyl, etc., are mentioned. The examples of the connecting group are not limited to the above.

Examples of the substituent that a coupling group derived from any one of the alkane, alkene, and atomatic ring may further contain include, of course not limited to: alkyl groups such as a methyl group, an ethyl group, and a propyl group; aryl groups such as a phenyl group and a biphenyl group; heterocyclic groups such as a thienyl group, a pyrrolyl group, and a pyridyl group; substituted amino groups such as a dimethylamino group, a diethylamino group, a dibenzylamino group, a diphenylamino group, a ditolylamino group, and a dianisolylamino group; halogen atoms such as fluorine, chlorine, bromine, and iodine.

$R_1$ to $R_9$ each independently represent a substituent selected from a hydrogen atom, a $C_{2\text{-}20}$ alkyl group, a substituted or unsubstituted alkenyl group, a substituted or unsubstituted alkynyl group, a silyl group, a substituted amino group, a substituted or unsubstituted aryl group having two or more rings, and a substituted or unsubstituted fused polycyclic heterocyclic group.

A specific example of a substituent which may be contained in an alkyl group, an alkenyl group, an alkynyl group, a silyl group, a substituted amino group, an aryl group, a heterocyclic group which are represented by $R_1$ to $R_9$; and the above-mentioned alkyl group, alkenyl group, alkynyl group, aryl group having two or more rings, and fused polycyclic heterocyclic group is the same as the specific example of the substituent represented by $R_1$ to $R_{10}$ in the benzo(ghi)fluoranthene derivative represented by General Formula (1).

$R_1$ to $R_9$ each may be the same or different.

In the benzo(ghi)fluoranthene derivatives represented by General Formulae (1) and (2), the hydrogen atom, which exists in a substituent, may be substituted with deuterium.

In the benzo(ghi)fluoranthene derivative of the present invention, a benzo(ghi)fluoranthene skeleton that is the main skeleton thereof shows high electron affinity. Therefore, the benzo(ghi)fluoranthene derivative of the present invention is a material having a deep LUMO level (the electron affinity is high) and high electron acceptability.

When, for example, a compound in which benzo(k)fluoranthene is substituted at $R_5$ position or $R_{10}$ position among the benzo(ghi)fluoranthene derivatives of the present invention is subjected to molecular orbital calculation, the following facts become clear. More specifically, it is revealed based on the fact that a benzo(k)fluoranethenyl group is substituted that the LUMO orbit of the compound itself extends to the acenaphthylene portion of the benzo(k)fluoranethenyl around the benzo(ghi)fluoranthene skeleton. Therefore, the LUMO level becomes deeper and electron trapping properties are improved. In contrast, it is revealed that the HOMO orbit of the compound itself extends to the naphthalene portion including the connecting position of the benzo(ghi)fluoranthene around the benzo(k)fluoranthene skeleton. The calculation results suggest that the electron trapping properties of all of the molecules of the benzo(ghi)fluoranthene derivative are high based on the extension of the LUMO orbit from the benzo(ghi)fluoranthene to the benzo(k)fluoranthene. It should be noted that the effect that the electron trapping properties increase is demonstrated similarly as in the case where the benzo(k)fluoranthene skeleton is introduced, even when a skeleton derived from a compound whose fluorescence quantum efficiency is higher than that of an unsubstituted benzo(ghi)fluoranthene is introduced. A specific example of the compound whose fluorescence quantum efficiency is higher than that of an unsubstituted benzo(ghi)fluoranthene will be mentioned later.

Moreover, when the benzo(ghi)fluoranthene derivative of the present invention is used as a component of a light emitting layer of an organic light emitting device, it is preferred that the light emission quantum efficiency of the light-emission center material itself be high in order to improve the light emitting efficiency of an organic light emitting device.

However, the fluorescence quantum efficiency of an unsubstituted benzo(ghi)fluoranthene is low. Thus, in order to increase the fluorescence quantum efficiency, it is necessary to introduce a certain substituent to the benzo(ghi)fluoranthene skeleton. Moreover, depending on the type of a substituent to be introduced, the fluorescence quantum efficiency can be sharply improved to thereby improve the light emitting efficiency of an organic light emitting device.

According to Steaven L. Murov, Ian Carmichael, Gordon L. Hug, Handbook of Photochemistry (1993), the fluorescence quantum efficiency of various compounds containing an unsubstituted benzo(ghi)fluoranthene are as shown in Table 1.

TABLE 1

| Compound | Fluorescence quantum efficiency |
|---|---|
| benzo(ghi)fluoranthene | 0.30 |
| P-terphenyl | 0.77 |
| Fluorene | 0.68 |
| Fluoranthene | 0.35 |
| benzo(k)fluoranthene | 1.0 |
| Pyrene | 0.65 |
| Perylene | 0.75 |
| Benzene | 0.06 |
| Triphenylamine | 0.045 |

Table 1 shows that, in order to improve the fluorescence quantum efficiency of the benzo(ghi)fluoranthene, a substituent defined as an aryl group which has two or more rings and which is represented by $R_1$ to $R_{10}$ in General Formula (1) or $R_1$ to $R_9$ in General Formula (2) may be introduced. In contrast, Table 1 shows that the effect of improving the fluorescence quantum efficiency of the benzo(ghi)fluoranthene is quite low even when benzene or amine is introduced. Therefore, the benzo(ghi)fluoranthene derivative in which benzene or a diphenylamino group is introduced into the benzo(ghi) fluoranthene skeleton is not suitable as a light emitting material.

In particular, based on the fact that especially tertiary amine, such as arylamine, is susceptible to oxidation, such a compound is unstable to oxygen. Therefore, a substituent derived from tertiary amine is not suitable as a substituent to be introduced into the benzo(ghi)fluoranthene skeleton.

Moreover, in the benzo(ghi)fluoranthene derivative of General Formula (1), a substituent is preferably introduced into any one of $R_5$ to $R_{10}$. This aims to improve the chemical stability by introducing a substituent into $R_5$ position and $R_{10}$ position based on the fact that $R_5$ position and $R_{10}$ position in the benzo(ghi)fluoranthene derivative of General Formula (1) show high reactivity.

As a substituent introduced into one of $R_5$ position and $R_{10}$ position, a fused polycyclic aromatic, group such as a pyrenyl group and fluorane thenyl group, or a fused polycyclic heterocyclic group is preferred. The fused polycyclic aromatic group and the fused polycyclic heterocyclic group are substituents that improve the fluorescence quantum efficiency of molecules themselves of the benzo(ghi)fluoranthene derivative as described above. Therefore, when the fused polycyclic aromatic group or the fused polycyclic heterocyclic group is substituted at one of $R_5$ and $R_{10}$, the effect of improving the fluorescence quantum efficiency is improved.

In the benzo(ghi)fluoranthene derivative represented by General Formula (2), a connecting group derived from the fused polycyclic aromatic group or the fused polycyclic heterocyclic group is preferably introduced as the connecting group represented by L. Thus, steric hindrance due to the peri position and an effect on rotation restraint are acquired, and the chemical stability can be increased similarly as in the benzo(ghi)fluoranthene derivative represented by General Formula (1). Moreover, by introducing the connecting group derived from the fused polycyclic aromatic group or the fused polycyclic heterocyclic group, the fluorescence quantum efficiency of the benzo(ghi)fluoranthene derivative itself is improved.

By introducing a bulky substituent, such as a tert-butyl group, steric hindrance occurs and concentration quenching resulting from the interaction of the fused cyclic aromatic groups between molecules is suppressed.

Specific structural formulae of the benzo(ghi)fluoranthene derivatives of the present invention are shown below. However, the typical examples of the benzo(ghi)fluoranthene derivatives of the present invention are merely shown, and the present invention is not limited to the following.

COMPOUND EXAMPLES 1

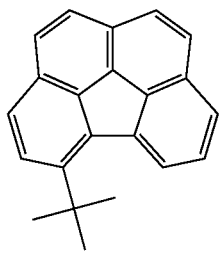

001

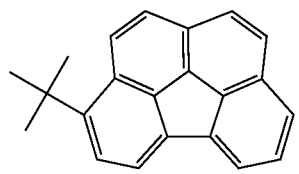

002

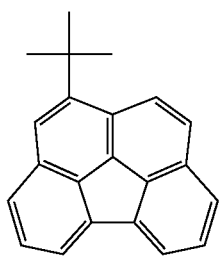

003

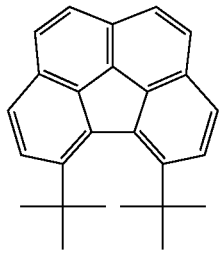

004

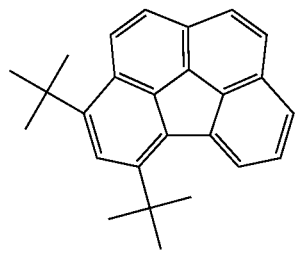

005

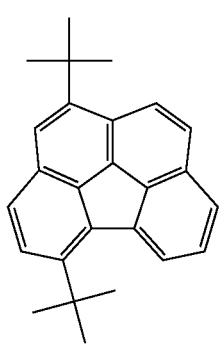

006

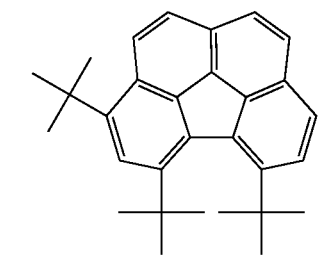
007
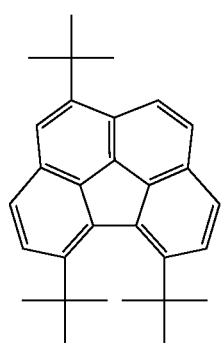
008
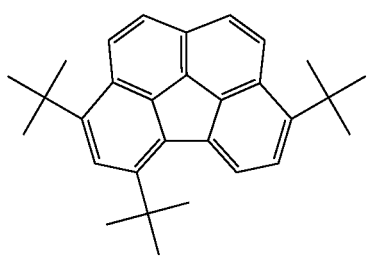
009
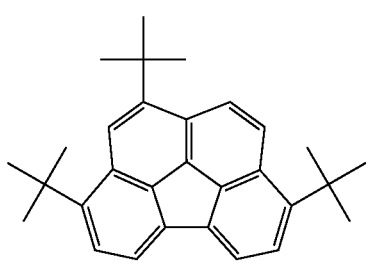
010
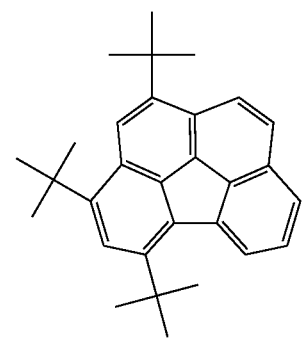
011
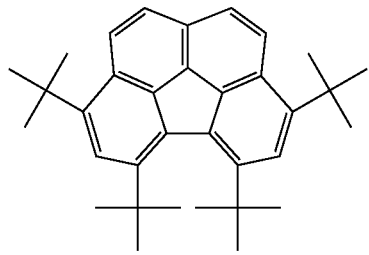
012
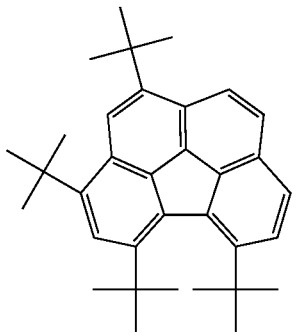
013
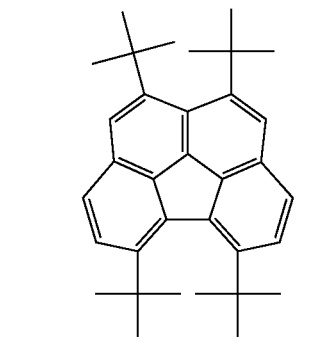
014
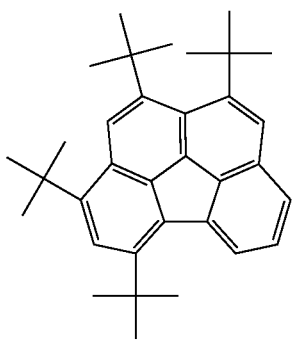
015
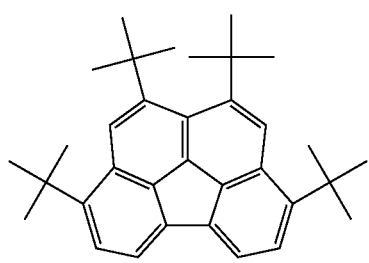
016

017
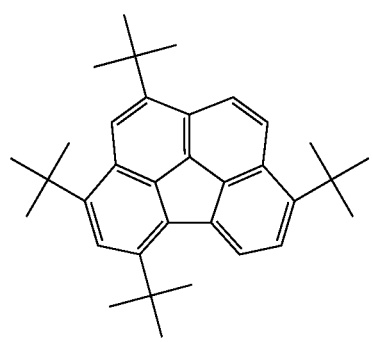
018
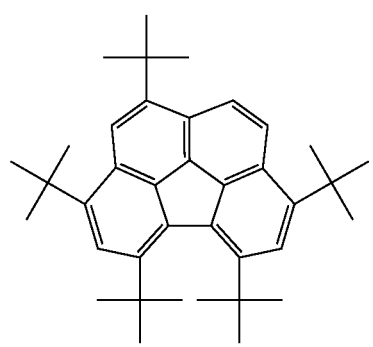
019
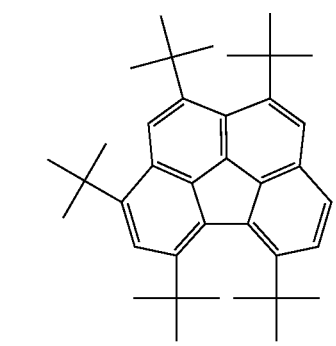
020
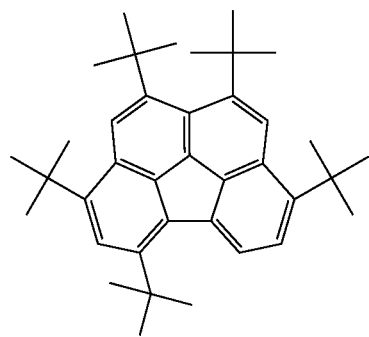
021
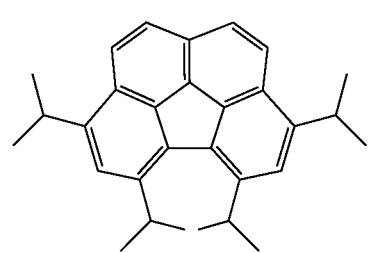
022
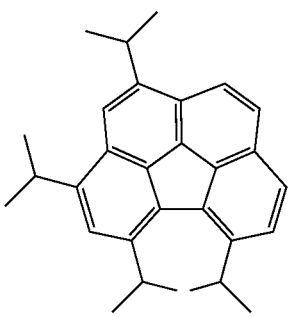
023
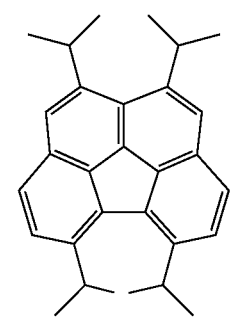
024
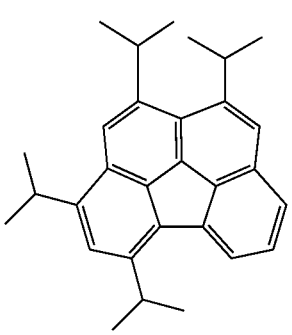
025
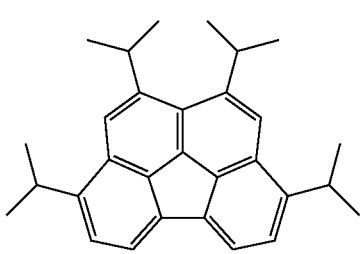
026
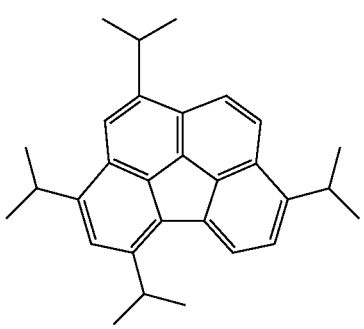

13
-continued
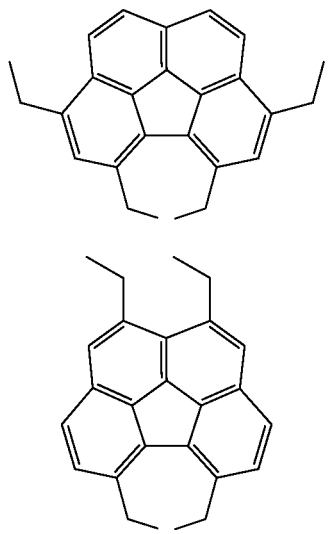
027
14
-continued
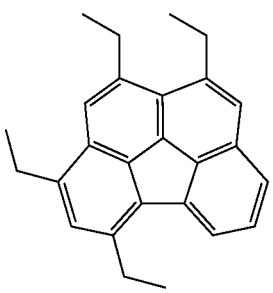
029
028
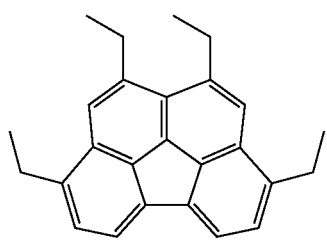
030
COMPOUND EXAMPLES 2
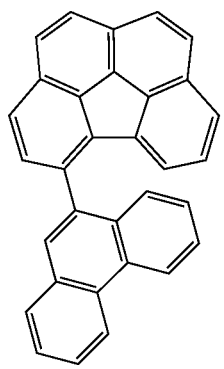
101
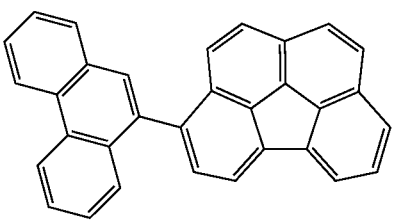
102
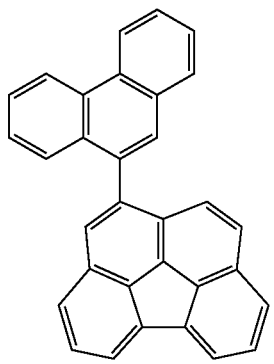
103
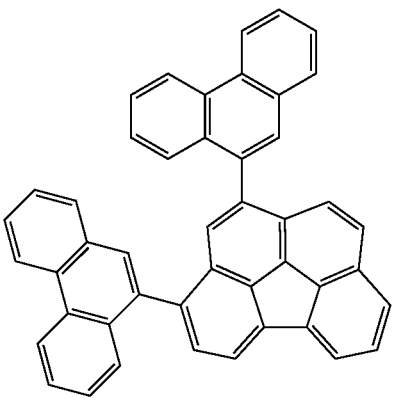
104

-continued
105
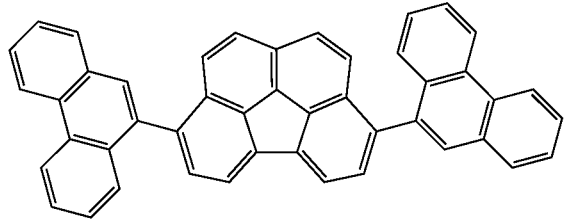
106
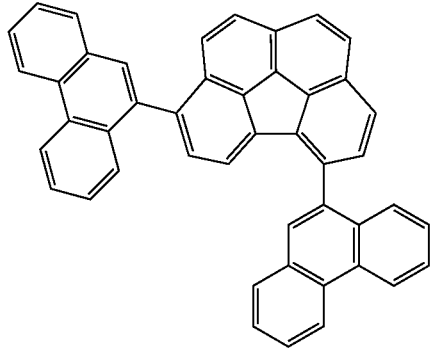
107
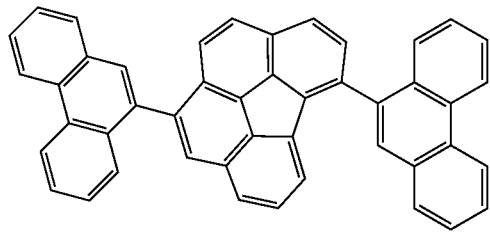
108
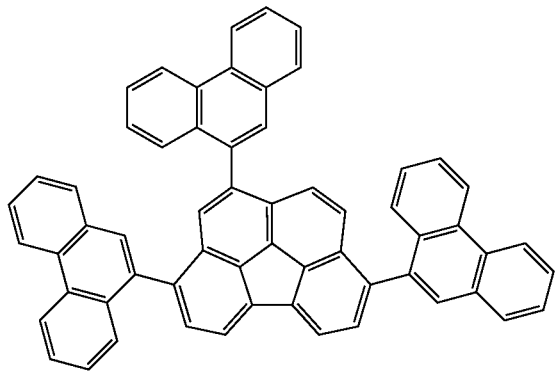
109
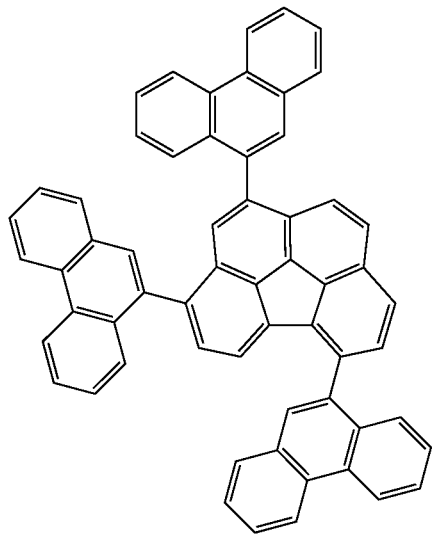
110
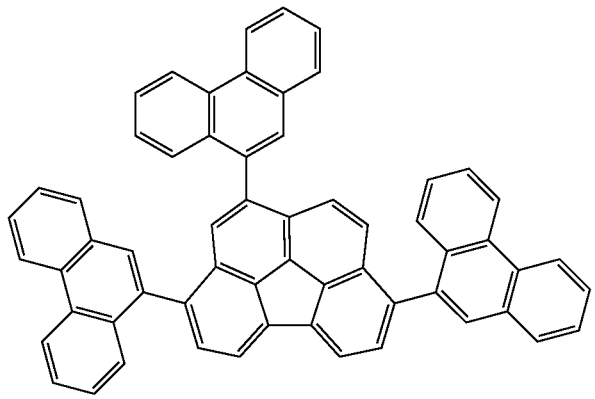

-continued
111 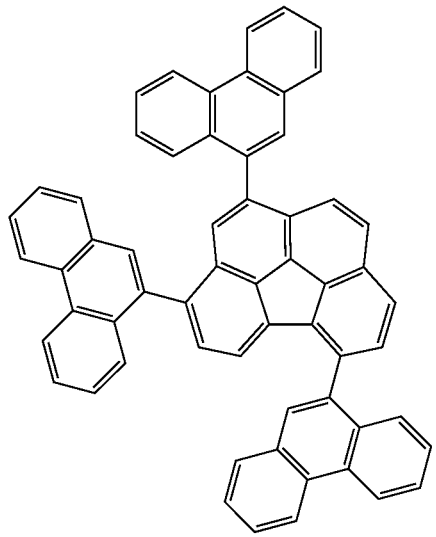
112 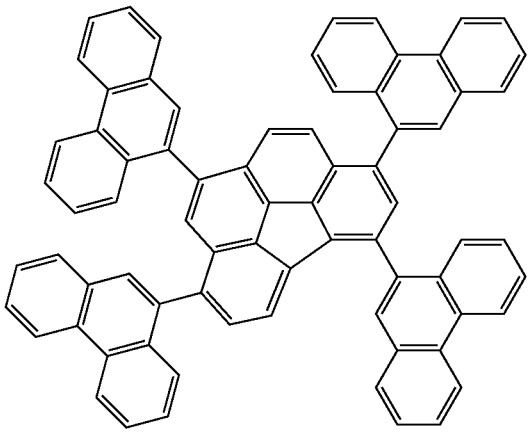
113 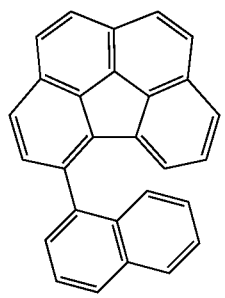
114 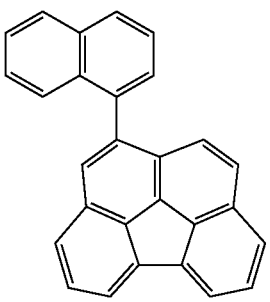
115 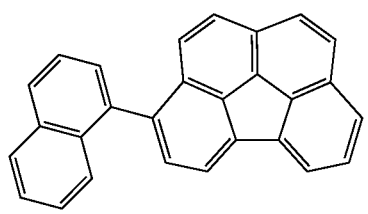
116 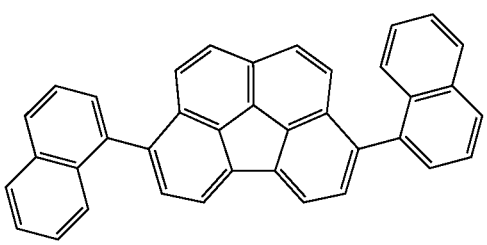
117 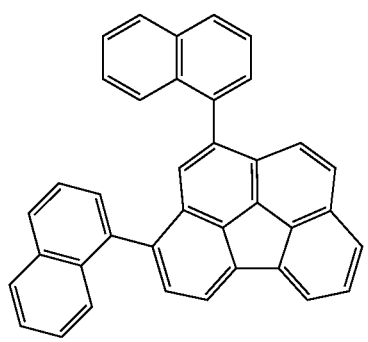
118 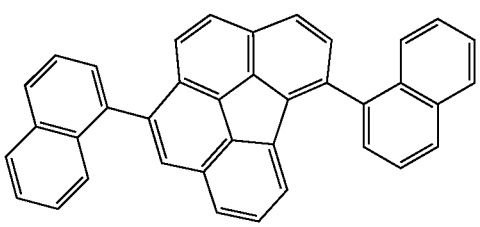

-continued
| | |
|---|---|
| 119 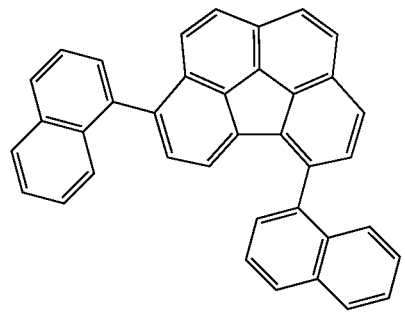 | 120 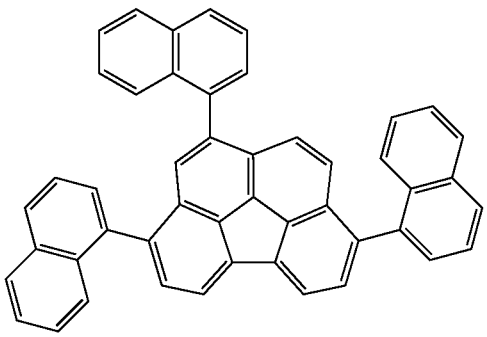 |
| 121 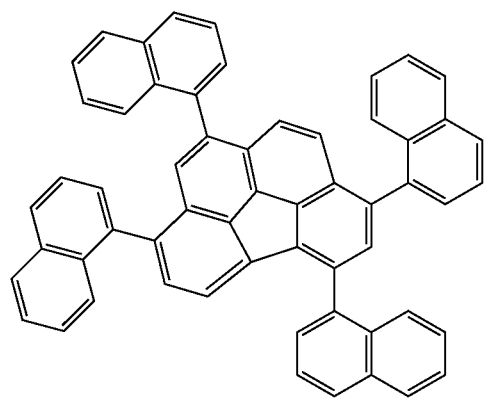 | 122 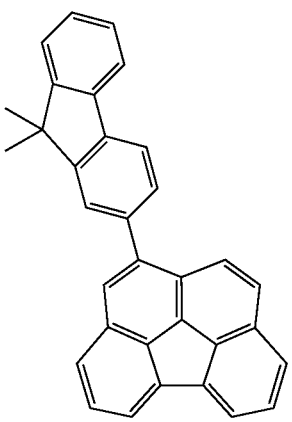 |
| 123 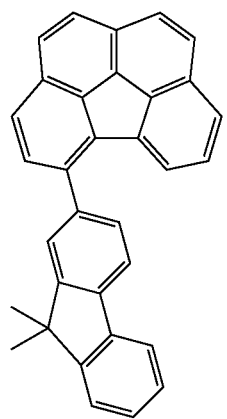 | 124 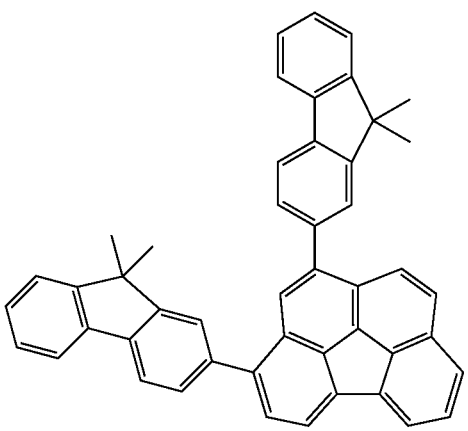 |
| 125 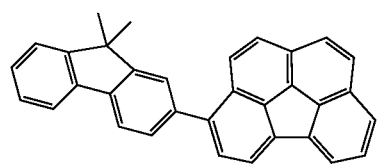 | 126  |

-continued
127
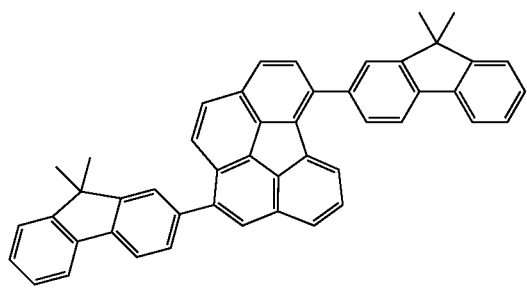
128
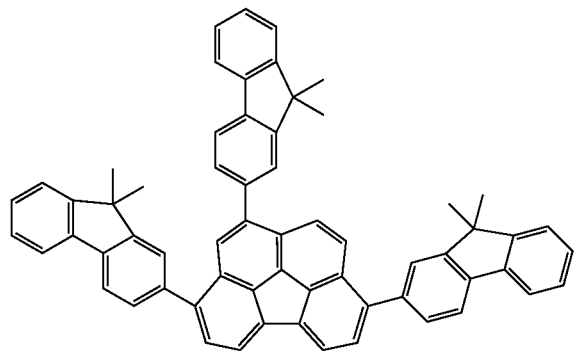
129
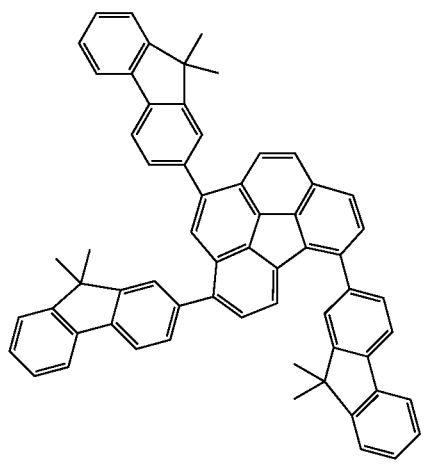
130
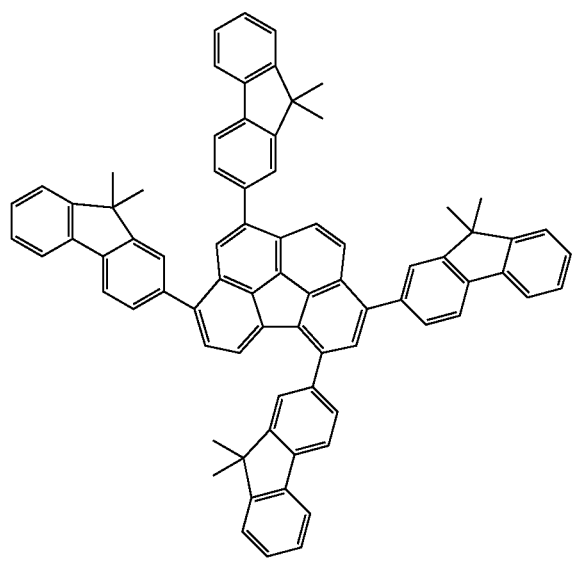
131
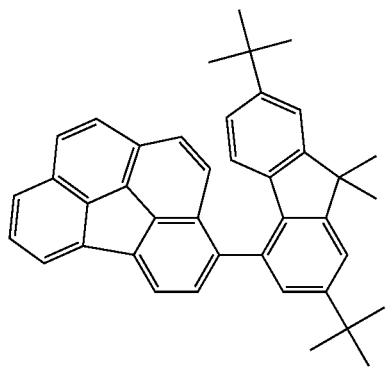
132
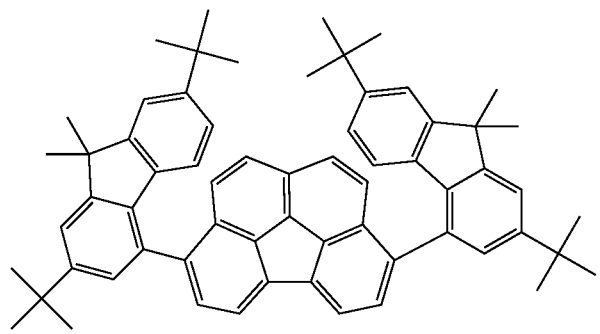
133
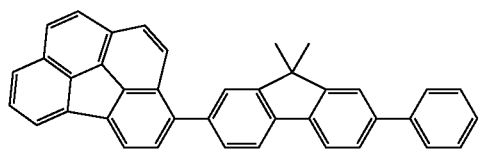
134
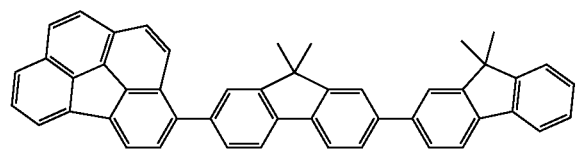

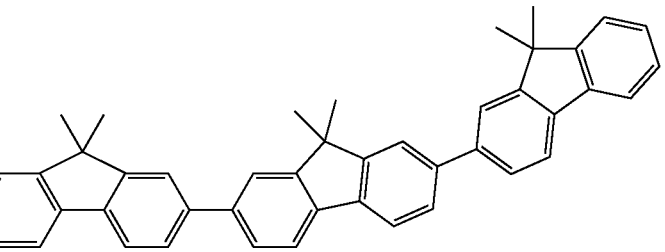
135
COMPOUND EXAMPLES 3
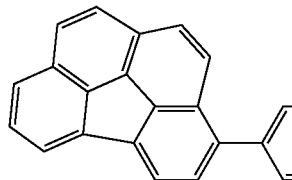
201
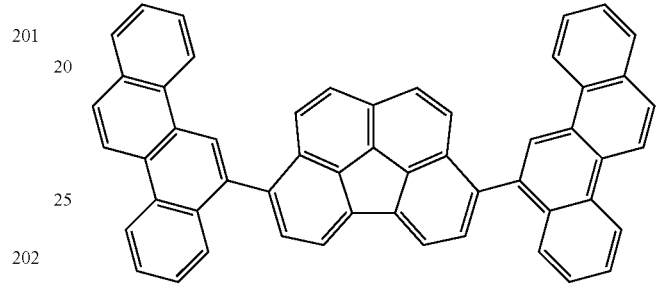
206
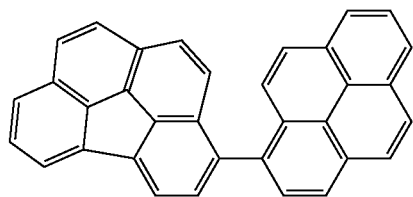
202
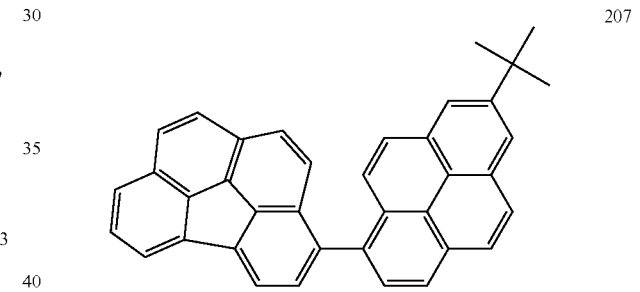
207
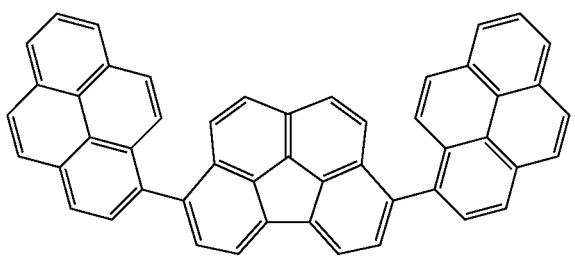
203
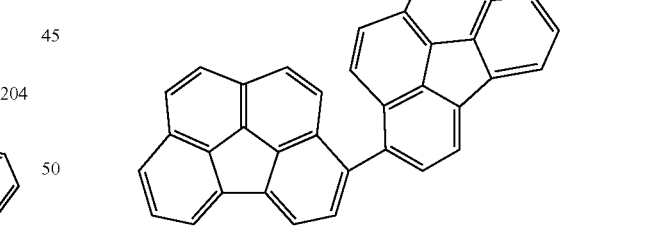
208
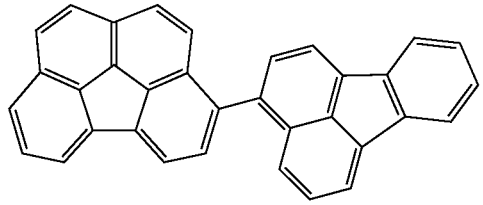
204
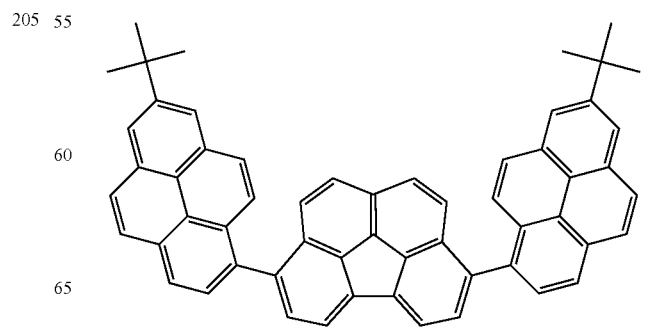
209
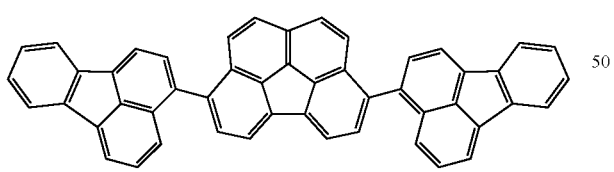
205
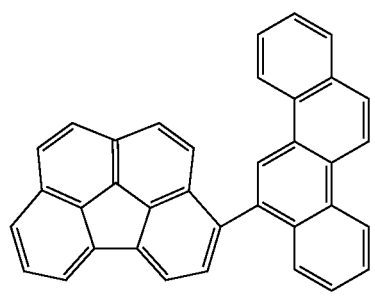

210
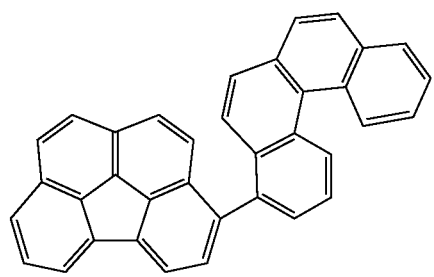
215
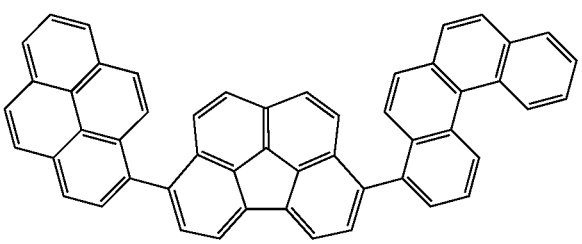
211
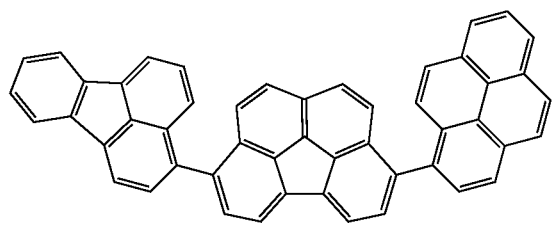
216
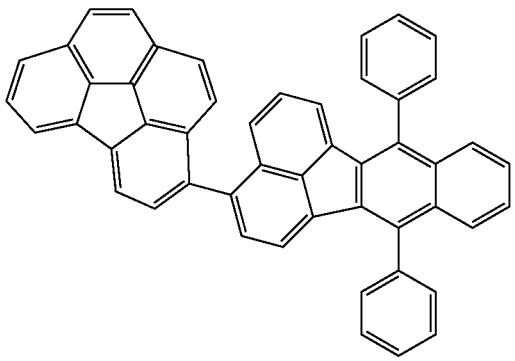
212
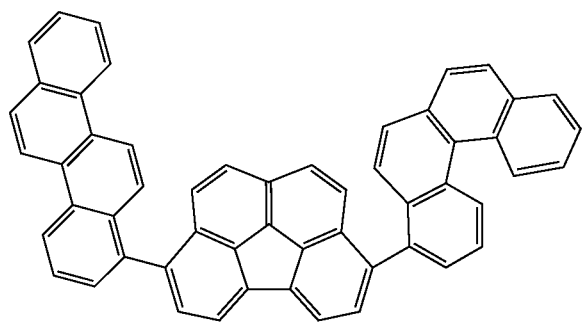
COMPOUND EXAMPLES 4
301
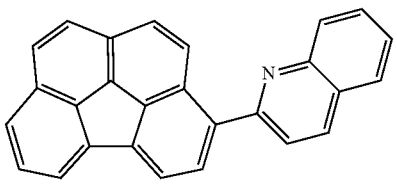
302
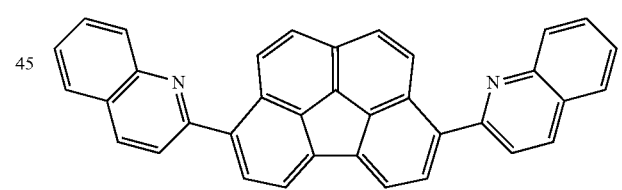
213
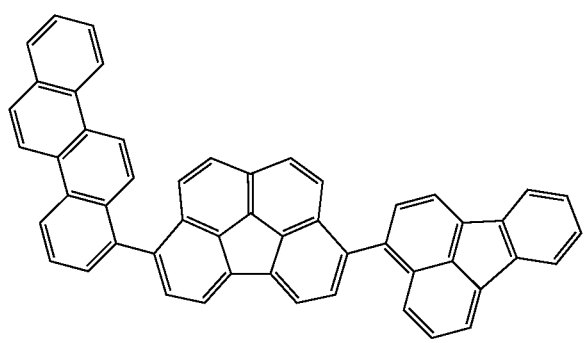
303
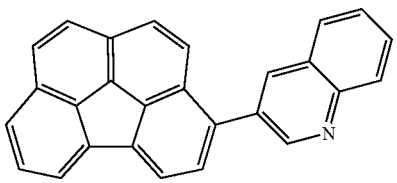
214
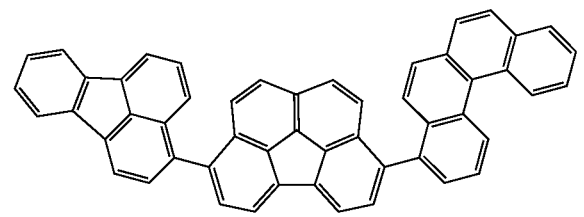
304
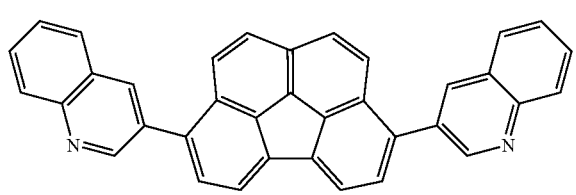

305
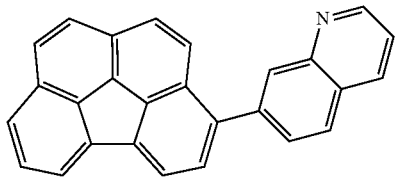
306
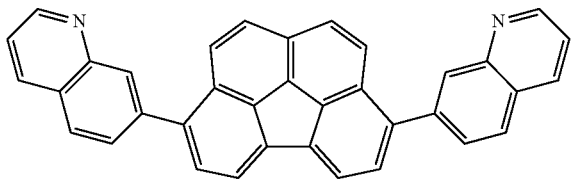
307
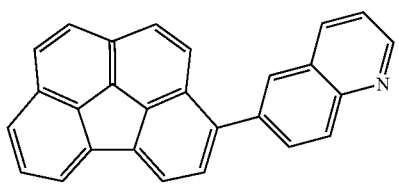
308
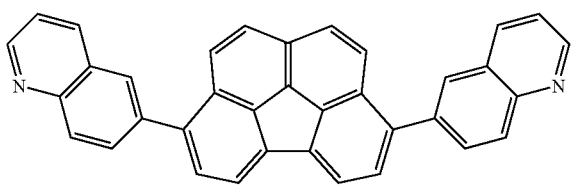
309
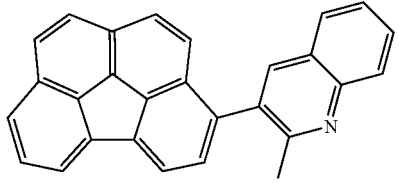
310
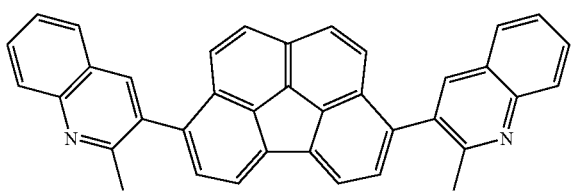
311
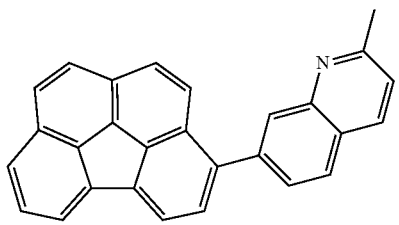
312
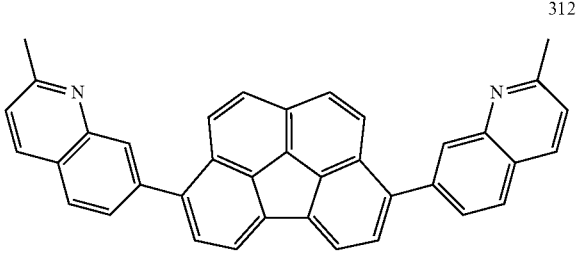
313
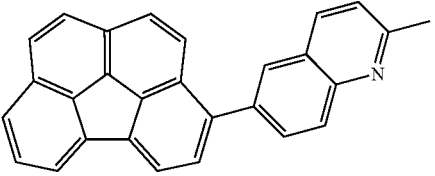
314
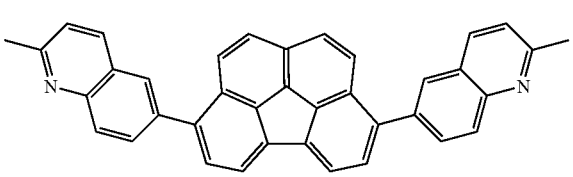
315
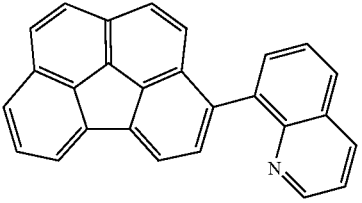
316
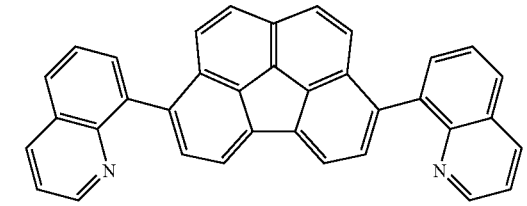
317
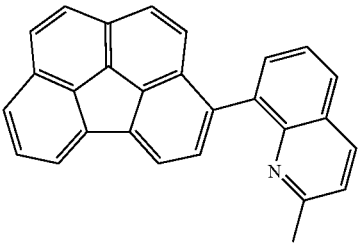
318
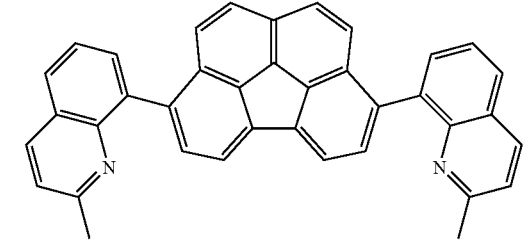

-continued 319
320
321
322
323
324
325

-continued 326
327
328
329
330
331
332
333

31
-continued
334
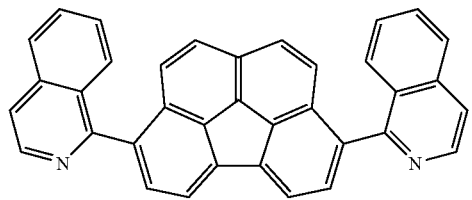
335
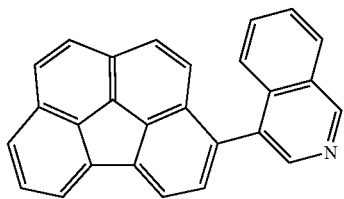
336
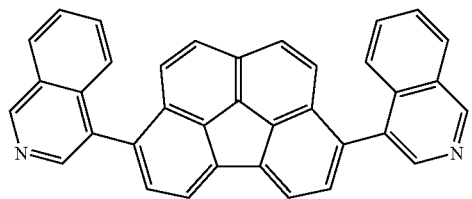
337
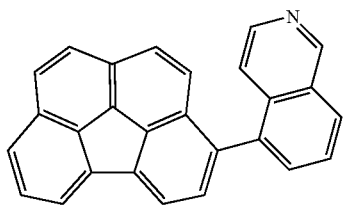
338
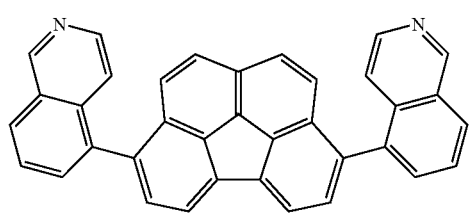
339
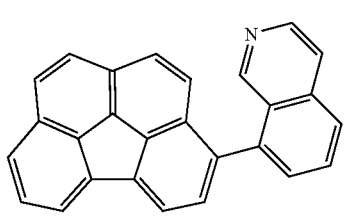
340
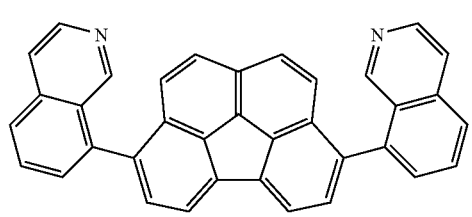
341
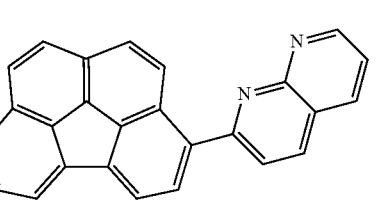
32
-continued
342
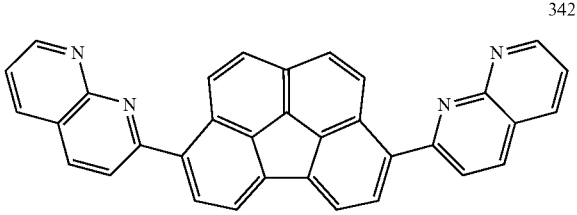
343
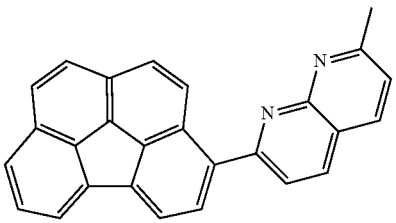
344
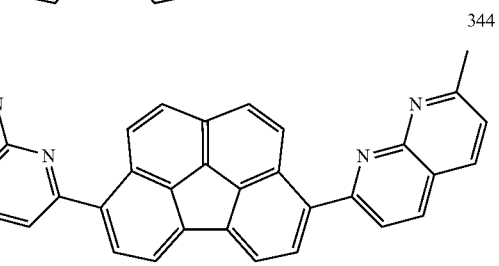
345
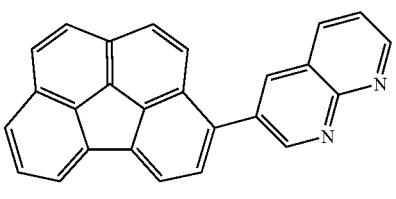
346
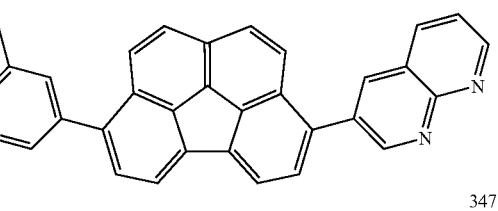
347
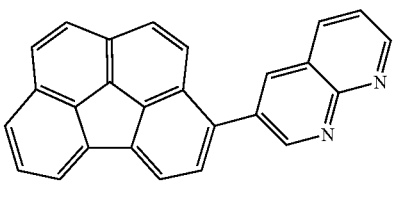
348
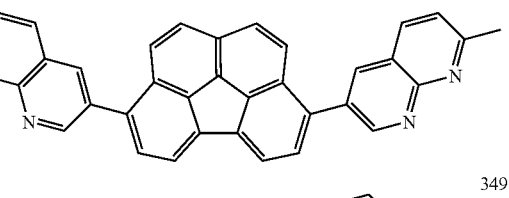
349
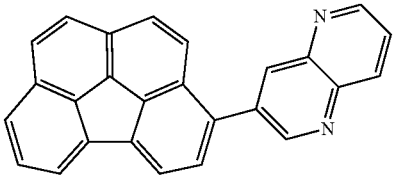

350
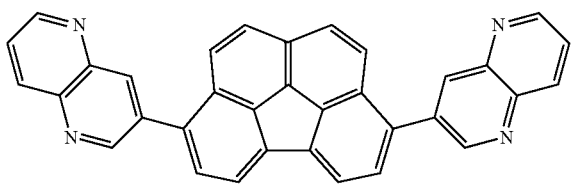
351
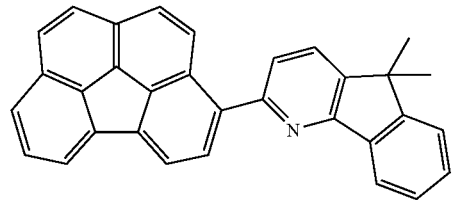
352
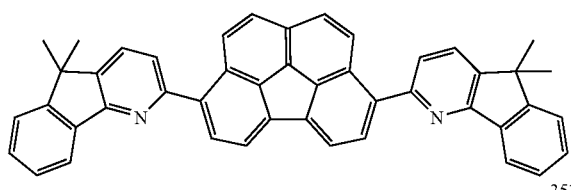
353
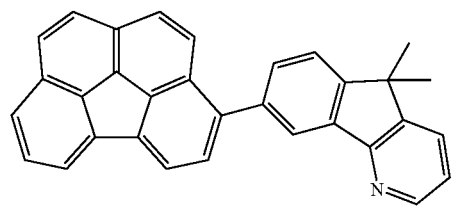
354
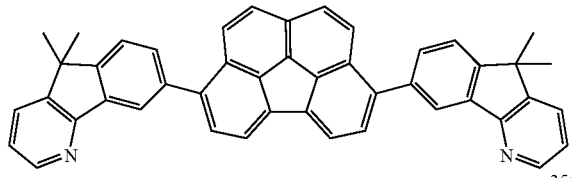
355
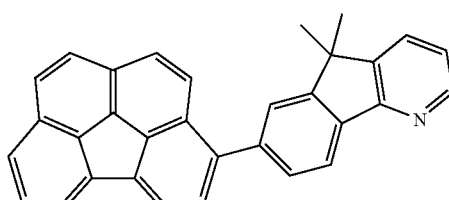
356
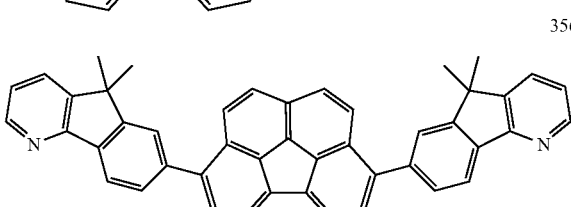
357
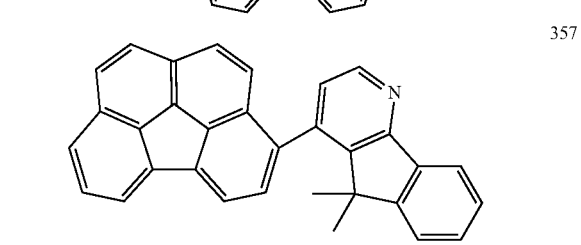
358
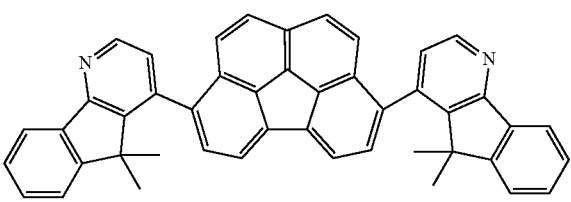
359
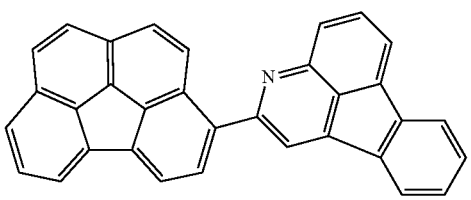
360
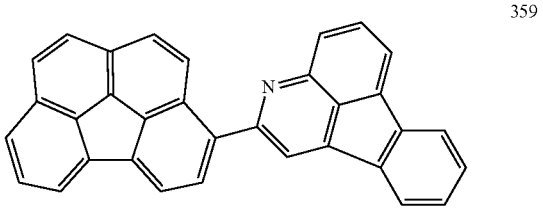
361
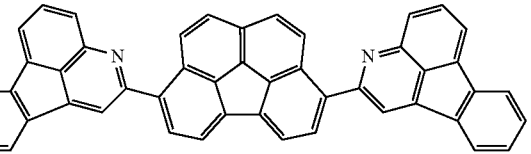
362
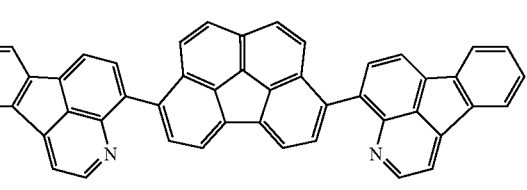
363
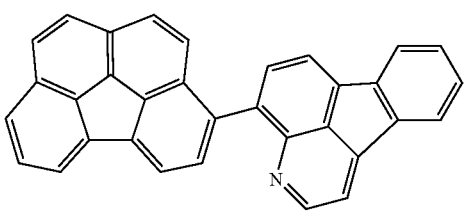
364
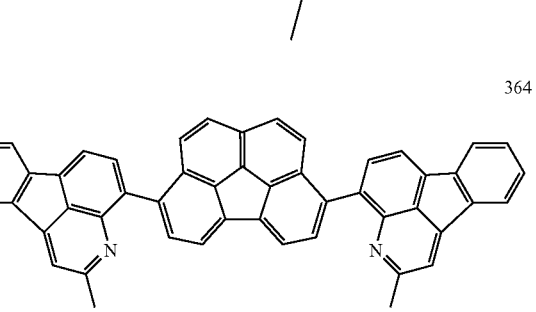

US 8,021,766 B2
35 -continued
365
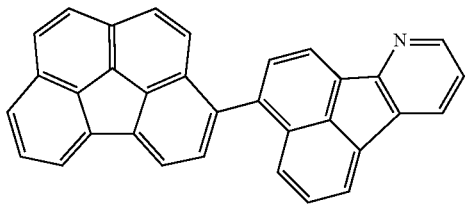
366
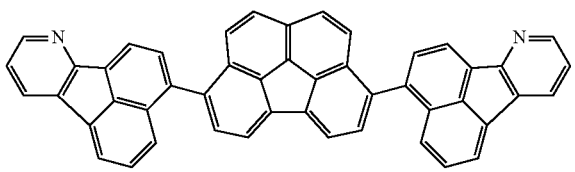
367
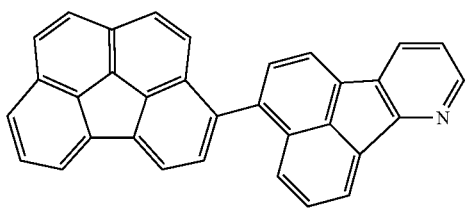
368
369
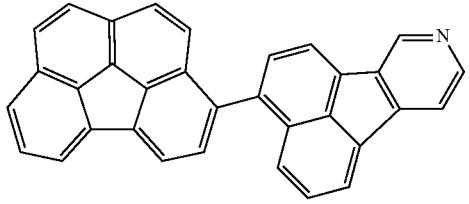
370
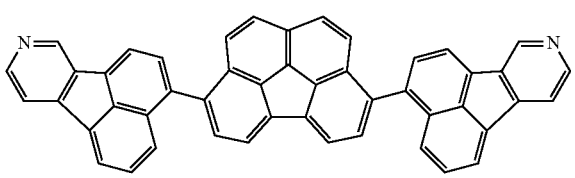
36 -continued
371
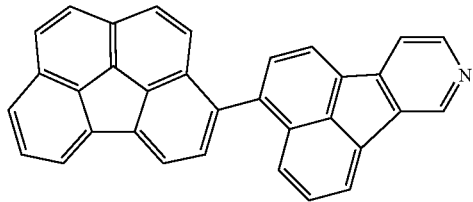
372
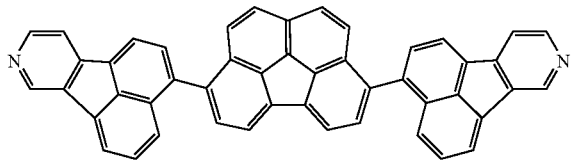
373
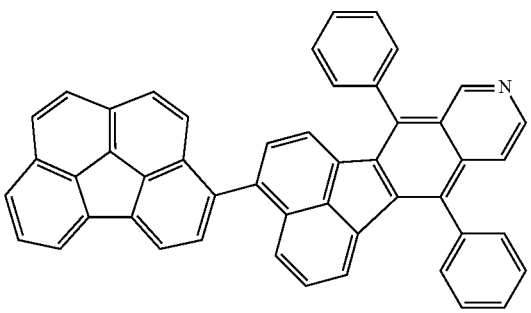
374
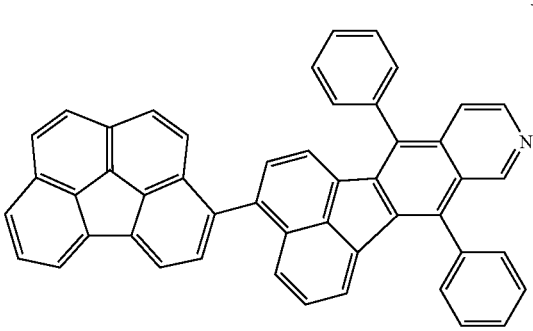
COMPOUND EXAMPLES 5
401
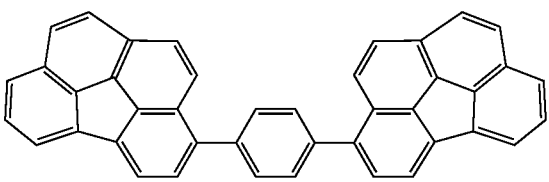
402
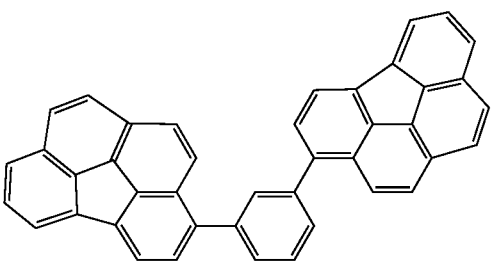

-continued
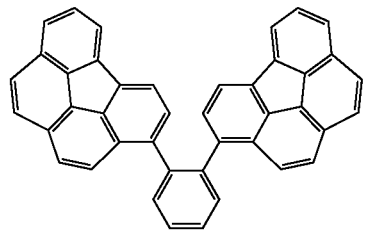
403
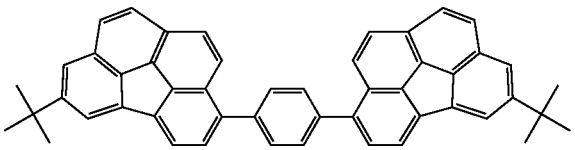
404
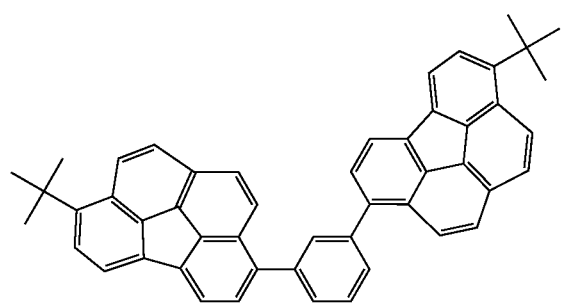
405
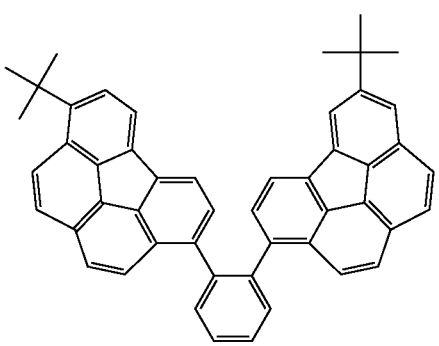
406
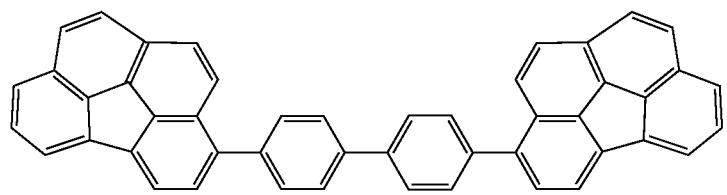
407
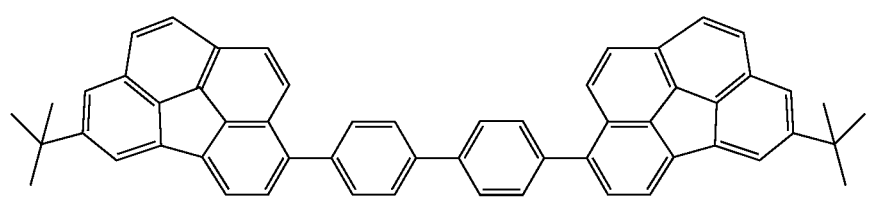
408
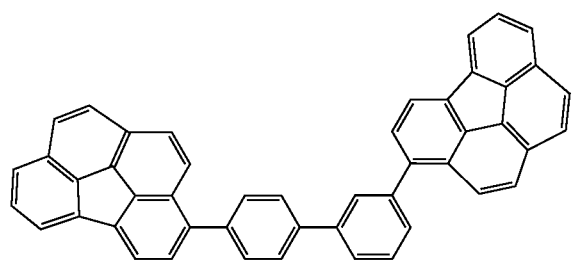
409
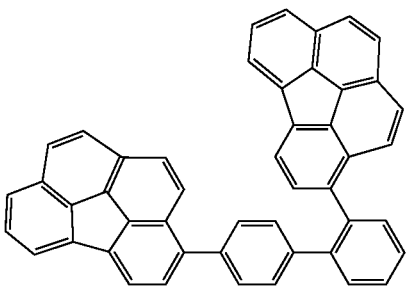
410

-continued
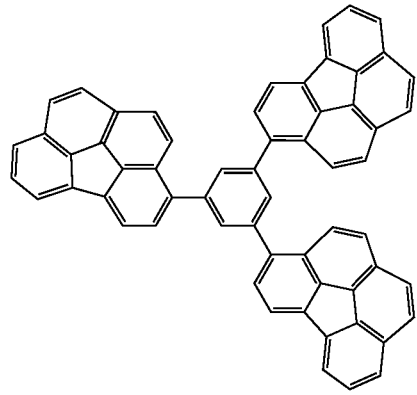 411
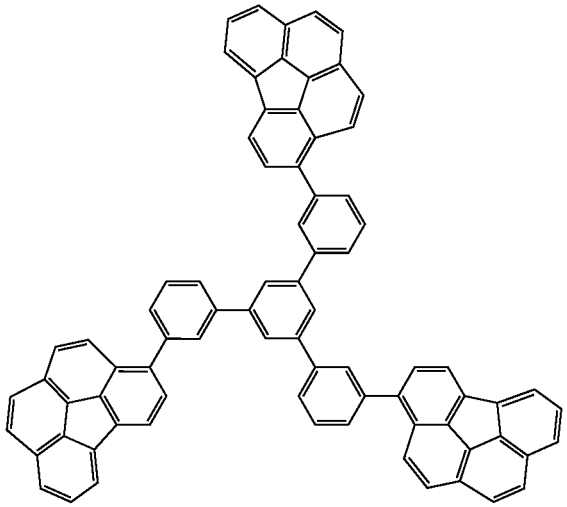 412
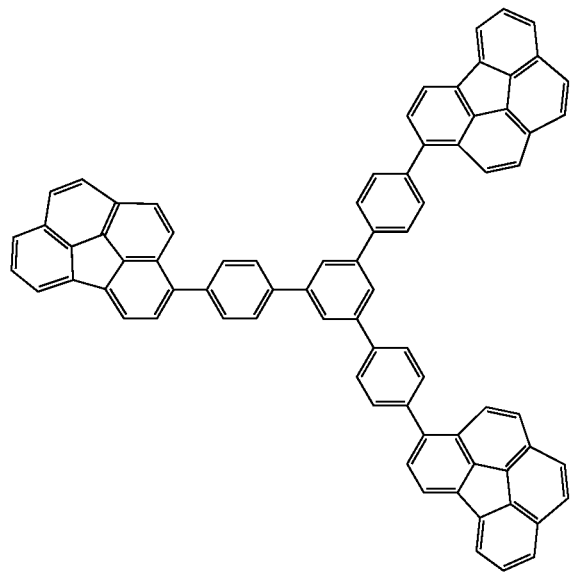 413
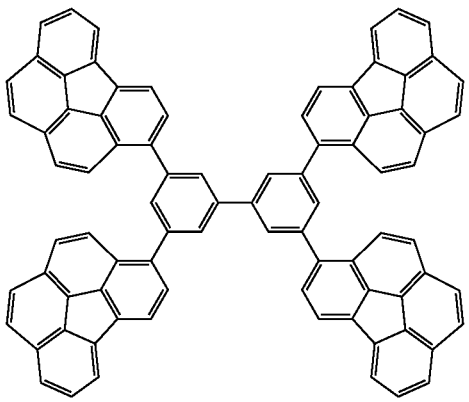 414
COMPOUND EXAMPLES 6
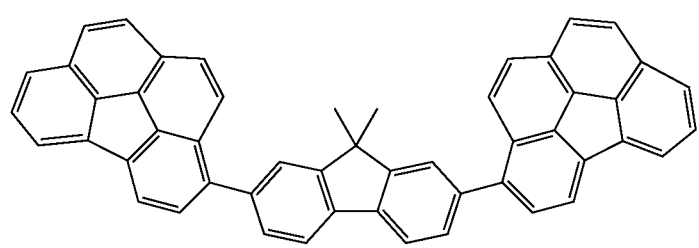 501

-continued
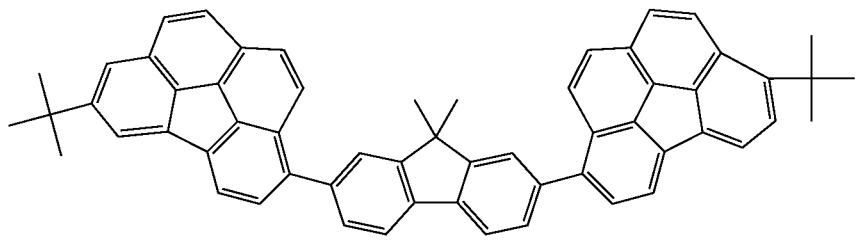
502
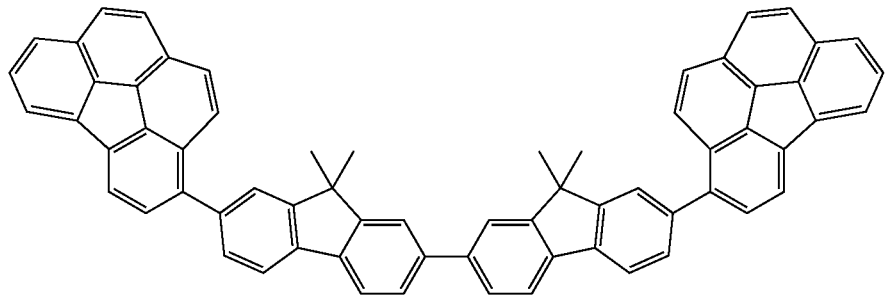
503
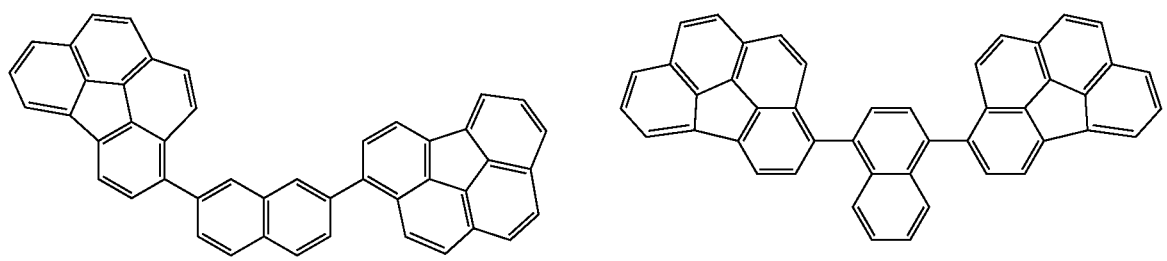
504 505
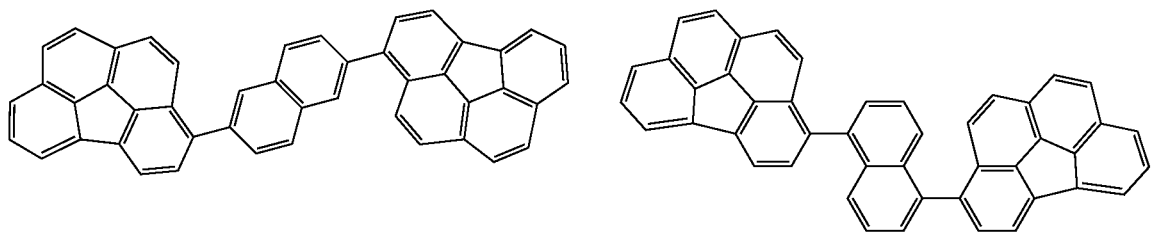
506 507
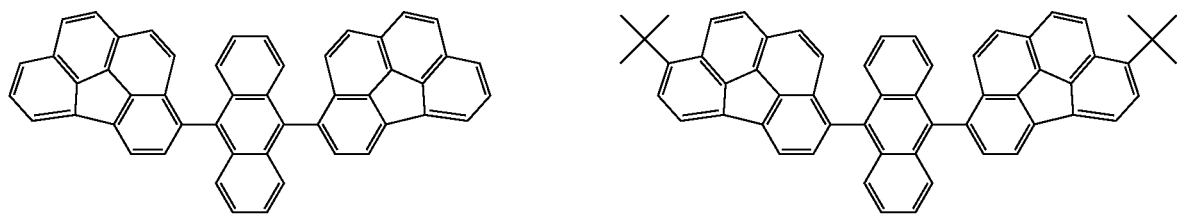
508 509
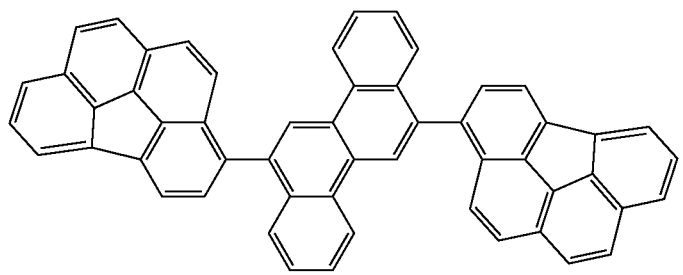
510

-continued

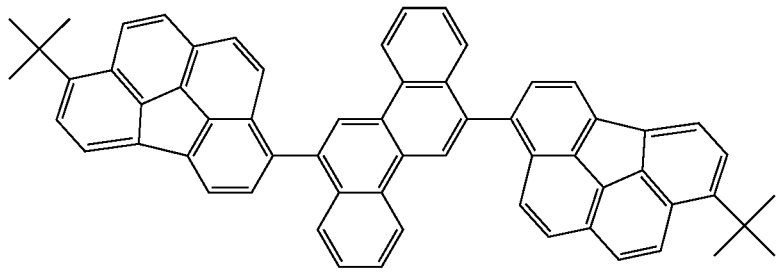

511

Next, the organic light emitting device of the present invention will be described in detail.

The organic light emitting device of the present invention includes a pair of electrodes having an anode and a cathode and at least one layer containing an organic compound sandwiched between the pair of electrodes. At least one of the anode and the cathode is transparent or translucent.

Hereinafter, an organic light emitting device of the present invention will be described in detail with reference to the drawings.

Reference Numerals of FIGS. 1 to 5 will be described first.

Reference Numeral 1 denotes a substrate; 2, an anode; 3, a light emitting layer; 4, a cathode; 5, a hole transporting layer; 6, an electron transporting layer; 7, a hole injecting layer; 8, a hole/exciton blocking layer; and 10, 20, 30, 40, and 50 each denote an organic light emitting device.

FIG. 1 is a sectional view illustrating a first embodiment of an organic light emitting device according to the present invention. The organic light emitting device 10 of FIG. 1 includes the anode 2, the light emitting layer 3, and the cathode 4, which are sequentially formed on the substrate 1. The organic light emitting device 10 is useful in a case where the light emitting layer 3 is formed of a compound which has all the properties including a hole transporting ability, an electron transporting ability, and light emitting property or a case where the light emitting layer 3 is formed of a mixture of compounds each having one of the hole transporting ability, the electron transporting ability, and the light emitting property.

Figure 2:
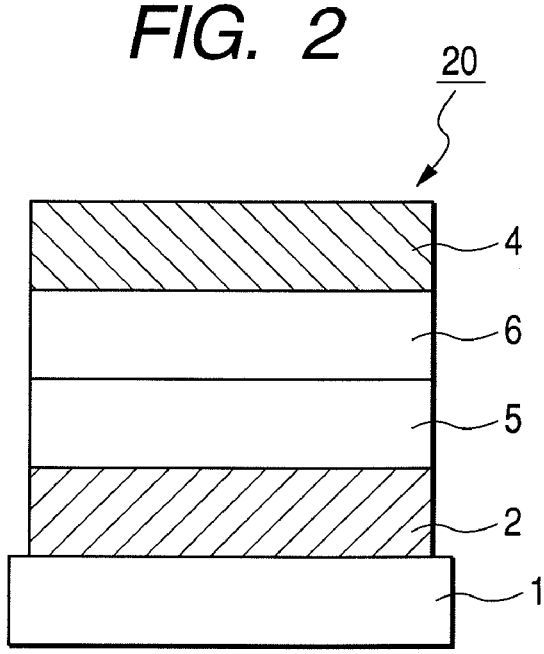
FIG. 2 is a cross sectional view illustrating an organic light emitting device according to a second Embodiment of the present invention.

FIG. 2 is a sectional view illustrating a second embodiment of the organic light emitting device according to the present invention. The organic light emitting device 20 of FIG. 2 includes the anode 2, the hole transporting layer 5, the electron transporting layer 6, and the cathode 4, which are sequentially formed on the substrate 1. The organic light emitting device 20 is useful in a case where a light emitting compound having one of hole transporting property and electron transporting property and an organic compound having electron transporting property alone or hole transporting property alone are used in combination. In addition, in the light emitting device 20, the hole transporting layer 5 or the electron transporting layer 6 serves as the light emitting layer.

Figure 3:
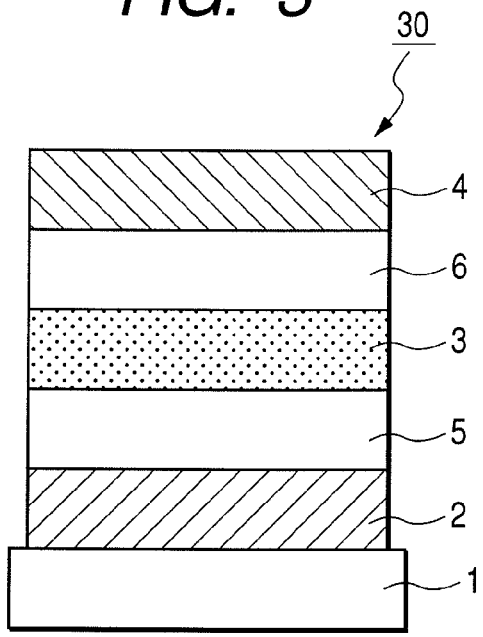
FIG. 3 is a cross sectional view illustrating an organic light emitting device according to a third Embodiment of the present invention.

FIG. 3 is a sectional view illustrating a third embodiment of the organic light emitting device according to the present invention. The organic light emitting device 30 of FIG. 3 illustrate a structure in which the light emitting layer 3 is inserted between the hole transporting layer 5 and the electron transport layer 6 in the organic light emitting device 20 of FIG. 2. In the organic light emitting device 30, a carrier transporting function and a light emitting function are separated from each other. Thus, the device can be used appropriately in combination with organic compounds each having one of the hole transporting property, electron transporting property, and light emitting property. Therefore, the degree of freedom in selection of a material extremely increases as well as various compounds different from each other in emission wavelength can be used. As a result, the range of luminescent colors can be widened. Further, a light emitting efficiency of the organic light emitting device 30 can be improved by effectively trapping carrier or exciton in the central light emitting layer 3.

Figure 4:
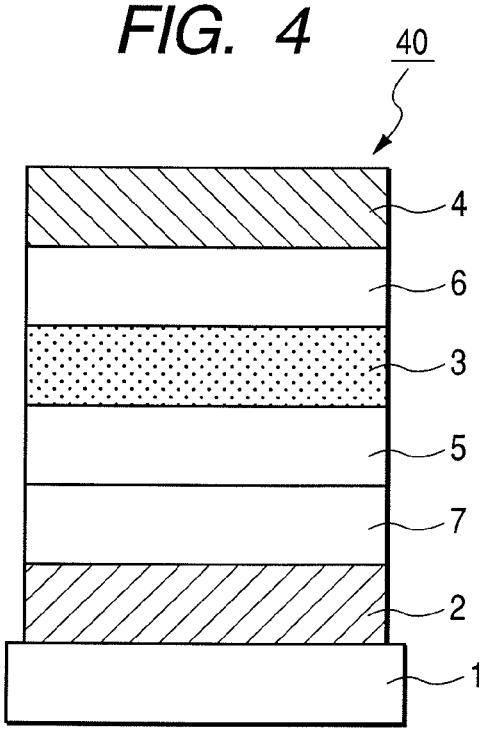
FIG. 4 is a cross sectional view illustrating an organic light emitting device according to a fourth Embodiment of the present invention.

FIG. 4 is a sectional view illustrating a fourth embodiment of the organic light emitting device according to the present invention. The organic light emitting device 40 of FIG. 4 illustrate a structure in which the hole injecting layer 7 is provided between the anode 2 and the hole transporting layer 5 in the organic light emitting device 30 of FIG. 3. The provision of the hole injecting layer 7 in the organic light emitting device 40 imparts an improving effect on adhesiveness between the anode 2 and the hole transporting layer 5 or on hole injection property, and is effective for a reduction in voltage at which the device is driven.

Figure 5:
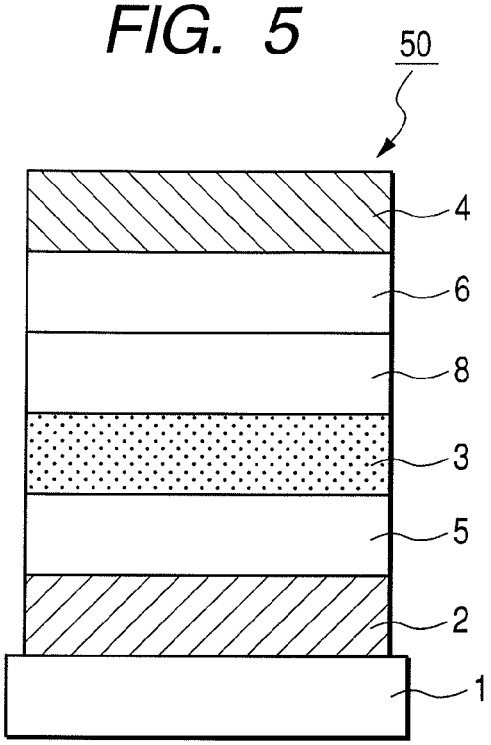
FIG. 5 is a cross sectional view illustrating an organic light emitting device according to a fifth Embodiment of the present invention.

FIG. 5 is a sectional view illustrating a fifth embodiment of the organic light emitting device according to the present invention. The organic light emitting device 50 of FIG. 5 illustrate a structure in which a layer for inhibiting the escape of a hole or exciton toward the side of the cathode 4 (hole/exciton blocking layer 8) is inserted between the light emitting layer 3 and the electron transporting layer 6 in the organic light emitting device 30 of FIG. 3. The use of a compound having an extremely high ionization potential as the hole/exciton blocking layer 8 improves the light emitting efficiency of the organic light emitting device 50.

It should be noted that the device structures illustrated in FIGS. 1 to 5 are each merely very basic one, and the structure of the organic light emitting device of the present invention is not limited to those. A variety of a layer structure may be provided. For example, an insulating layer may be provided onto an interface between an electrode and an organic layer, an adhesive layer or an interference layer may be provided thereonto, and a hole transporting layer may be formed of two layers having different ionization potentials.

The organic light emitting device of the present invention can be used in any forms illustrated in FIGS. 1 to 5.

The organic light emitting device containing the benzo(ghi)fluoranthene derivative of the present invention achieves high-luminance light emission with a low applied voltage and is excellent also in durability. In particular, an organic light emitting device using the benzo(ghi)fluoranthene derivative for a guest of a light emitting layer exhibits outstanding effects. More specifically, the light emission of blue light having a light emission peak of 430 nm or more to 470 nm or less is developed by a suitable molecular modification. Further, such an organic light emitting device achieves a high luminance with a low applied voltage and is excellent in durability.

It is preferred, in the organic light emitting device of the present invention, that the light emitting layer 3, the electron transporting layer 6, or the hole transporting layer 7 has at least one kind of the benzo(ghi)fluoranthene derivative of the present invention. It is more preferred that the light emitting layer 3 include the benzo(ghi)fluoranthene derivative of the present invention. The light emitting layer 3 preferably includes a host and a guest.

When the above-mentioned benzo(ghi)fluoranthene derivative is used as a material for an organic light emitting device forms the light emitting layer, the above-mentioned benzo(ghi)fluoranthene derivative can be used singly or as a dopant (guest) material or a host material.

When the light emitting layer is formed of a carrier transporting host material and guest material, the main process for light emission includes the following several steps.
 1. Transport of electron and hole in light emitting layer
 2. Production of exciton of host
 3. Transfer of excitation energy between host molecules
 4. Transfer of excitation energy from host to guest Desired energy transfer or light emission in each step occurs in competition with various deactivation steps.

It is needless to say that the light emission quantum efficiency of a light emitting center material itself must be large in order to increase the light emitting efficiency degree of the organic light emitting device. However, the efficiency of energy transfer between a host and another host or between a host and a guest is also a large problem to increase the light emitting efficiency of the organic light emitting device. On the other hand, the cause for the deterioration of light emission owing to energization has not yet been clarified. However, the deterioration is probably related to at least environmental changes to a light emitting material due to the light emitting center material or molecules around the center material.

Thus, when the benzo(ghi)fluoranthene derivative of the present invention is used especially as the host or the guest of the light emitting layer, the light emitting efficiency of the organic light emitting device is improved, high luminance is held over a long period of time, and deterioration of light emission due to energization decreases.

As one of specific reasons for the deterioration of light emission due to energization, the deterioration of light emission due to the deterioration in the thin film form of the light emitting layer is possibly mentioned. The deterioration of the thin film form possibly originates from crystallization of the organic thin film due to the temperature of a driving environment, heat development caused by driving the device, etc. This possibly results from the lowness of the glass transition temperature of a material. Thus, it is desired for the organic light emitting material to have a high glass transition temperature. Here, since the benzo(ghi)fluoranthene derivative of the present invention has a high glass transition temperature, increase in the durability of the organic light emitting device can be expected.

When the benzo(ghi)fluoranthene compound represented by General Formulae (1) and (2) is used as the host, the content thereof is 20 to 99.9 wt % based on a total amount of a material forming a light emitting layer.

When the benzo(ghi)fluoranthene compound represented by General Formulae (1) and (2) is used as a dopant (guest), the concentration of the dopant is 0.01 to 80 wt %, and preferably 1 to 40 wt % based on the concentration of the host material. The dopant material may be uniformly included throughout the layer containing the host material and may have a concentration gradient. By partially incorporating the dopant material into a certain area, the host material layer may have an area where no dopant material is included.

The organic light emitting device of the present invention uses the benzo(ghi)fluoranthene derivative represented by General Formulae (1) and (2) especially as a material forming the light emitting layer. Moreover, in addition to the benzo(ghi)fluoranthene derivative, a hole-transporting material, a light emitting material, an electron transporting material, or the like, which are low molecular-based or polymer-based material and are conventionally known, may be used together as required.

Those compounds will be exemplified below.

A preferred hole-injection transporting material has excellent mobility to facilitate the injection of a hole from an anode and to transport the injected hole to a light emitting layer. As low molecular and high molecular materials having hole-injecting and transporting abilities include, but are of course not limited to, a triarylamine derivative, a phenylene diamine derivative, a triazole derivative, an oxadiazole derivative, an imidazole derivative, a pyrazoline derivative, a pyrazolone derivative, an oxazole derivative, a fluorenone derivative, a hydrazone derivative, a stilbene derivative, a phthalocyanine derivative, a porphyrin derivative, and poly(vinylcarbazole), poly(silylene), poly(thiophene), and other conductive polymers.

As light emitting materials other than the above benzo[ghi]fluoranthene derivative, the following compounds can be given. Specific examples of the compounds include, but are of course not limited to, polycyclic condensed aromatic compounds (including naphthalene derivatives, phenanthrene derivatives, fluorene derivatives, pyrene derivatives, tetracene derivatives, coronene derivatives, chrysene derivatives, perylene derivatives, 9,10-diphenylanthracene derivatives, and rubrene); quinacridone derivatives; acridone derivatives; coumarin derivatives; pyran derivatives; Nile red; pyrazine derivatives; benzoimidazole derivatives; benzothiazole derivatives; benzoxazole derivatives; stilbene derivatives; organometallic complexes (including organic aluminum complexes such as tris(8-quinolinolato)aluminum, and organic beryllium complexes); and high-molecular derivatives such as poly(phenylene vinylene) derivatives, poly(fluorene) derivatives, poly(phenylene) derivatives, poly(thienylene vinylene) derivatives, and poly(acetylene) derivatives.

The electron-injection transporting material may be arbitrarily selected from compounds each of which facilitates the injection of an electron from a cathode and has a function of transporting the injected electron to a light emitting layer. In addition, the material is selected in consideration of, for example, a balance with the carrier mobility of the hole transporting material. The materials having electron-injection transporting abilities include, but are of course not limited to, an oxadiazole derivative, an oxazole derivative, a thiazole derivative, a thiadiazole derivative, a pyrazine derivative, a triazole derivative, a triazine derivative, a perylene derivative, a quinoline derivative, a quinoxaline derivative, a fluorenone derivative, an anthrone derivative, a phenanthroline derivative, and an organometallic complex.

Next, other materials used in the construction of the organic light emitting device of the present invention will be described.

A desirable anode material has as large a work function as possible. Examples of available materials include: metal elements such as gold, platinum, silver, copper, nickel, palladium, cobalt, selenium, vanadium, and tungsten, and alloys thereof; and metal oxides such as tin oxide, zinc oxide, indium oxide, indium tin oxide (ITO), and indium zinc oxide. Further, conductive polymers such as polyaniline, polypyrrole, polythiophene, and polyphenylene sulfide may also be used. Each of those electrode substances may be used singly. Alternatively, two or more of them may also be used in combination. Further, the anode may adopt any one of a single layer construction and a multilayer construction.

On the other hand, a desirable cathode material has as small a work function as possible. Examples of available materials include: metal elements such as lithium, sodium, potassium, calcium, magnesium, aluminum, indium, ruthenium, titanium, manganese, yttrium, silver, lead, tin, and chromium. Alternatively, those metal elements may be used in combination as alloys. For example, the following alloys can be used: lithium-indium, sodium-potassium, magnesium-silver, aluminum-lithium, aluminum-magnesium, and magnesium-indium alloys. Further, metal oxides such as indium tin oxide (ITO) may also be used. Each of those electrode substances may be used singly or in combination of two or more. Further, the cathode may adopt any one of a single layer construction and a multilayer construction.

Substrates which may be used in the organic light emitting device of the present invention include: opaque substrates such as metallic substrates and ceramics substrates; and transparent substrates such as glass, quartz, and plastic sheet substrates, but are not particularly limited to these materials. In addition, a color filter film, a fluorescent color converting film, a dielectric reflection film, or the like may be used in the substrate to control emitted light.

Furthermore, a protective layer or a sealing layer may be formed on the prepared device to prevent the device from contacting with oxygen, moisture, or the like. As the protective layer may be a diamond thin film, a film made of an inorganic material such as metal oxide or metal nitride, a polymer film made of a fluorine resin, polyparaxylene, polyethylene, silicone resin, polystyrene resin, or the like, or may be a photo-curing resin, or the like. Furthermore, the device itself can be covered with glass, an airtight film, metal, or the like and packaged with an appropriate sealing resin.

The device of the present invention can also be produced by being connected to a thin-film transistor (TFT) produced on a substrate.

Moreover, with respect to a direction of extracting light of the device, both a bottom emission structure (structure in which light is extracted from the substrate side) and a top emission structure (structure in which light is extracted from a side opposite to the substrate) can be acceptable.

In the organic light emitting device of the present invention, a layer containing a benzo(ghi)fluoranthene compound and a layer containing another organic compound are formed by a method described below. In general, such layers are produced using a vacuum vapor deposition method, ionization-assisted deposition method, a sputtering method, and a plasma method. In particular, a layer formed by the vacuum vapor deposition method, a solution coating method, or the like is preferred because crystallization is less likely to occur and has excellent stability with time. A thin film may be formed by dissolving the compound in a suitable solvent and subjecting the resultant to a known coating method (e.g., a spin coating method, a dipping method, a casting method, an LB method, an ink jet method, etc.). In film formation by the coating method, in particular, a film may be formed by using a compound in combination with an appropriate binder resin.

The above binder resins can be chosen from a wide variety of binder resins. Examples thereof include, but are not limited to, polyvinylcarbazole resins, polycarbonate resins, polyester resins, polyallylate resins, polystyrene resins, ABS resins, polybutadine resins, polyurethane resins, acrylic resins, methacrylic resins, butyral resins, polyvinyl acetal resins, polyamide resins, polyimide resins, polyethylene resins, polyethersulfone resins, diallyl phthalate resins, phenol resins, epoxy resins, silicone resins, polysulfone resins, and urea resin. Each of those may also be used singly. Alternatively, two or more of them may be mixed in combination as copolymers. Further, additives such as known plasticizers, antioxidants, and ultraviolet absorbers may be used together with the binder resins, if required.

Hereinafter, the present invention will be further specifically described with reference to Examples, but is not limited thereto.

EXAMPLE 1

Method of Producing tert-butyl Substituent of benzo(ghi)fluoranthene

A tert-butyl-4-substituted benzo(ghi)fluoranthene derivative and a tert-butyl-5-substituted benzo(ghi)fluoranthene derivative which are used in the organic light emitting device of the present invention was produced by a method described below.

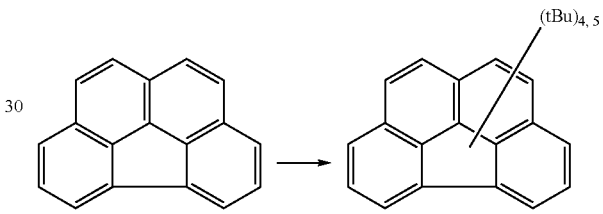

200 mg (0.88 mmol) of benzofluoranthene was dissolved in 20 ml of tert-butyl chloride under an argon atmosphere. 20 mg (0.12 mmol) of aluminum chloride was added to the solution, and then the mixture was heated at 49° C. for 3 hours. While observing the disappearance of a raw material by HPLC (high performance liquid chromatography), 5 ml of tert-butyl chloride and 60 mg (0.36 mmol) of aluminum chloride were further added. After confirming the disappearance of the raw material, the resultant was cooled to room temperature, poured in 100 ml of saturated sodium bicarbonate water, and extracted with ethyl acetate. The extracted organic layer was washed with water and a saturated sodium chloride solution in this order, dried over sodium sulfate, and then condensed to thereby obtain an yellow oily mixture. Next, the oily substance was purified by column chromatography. Thus, 170 mg of a fraction (Fr1) in which a tert-butyl-4-substituted material was a main component and 190 mg of a fraction (Fr2) in which a tert-butyl-5-substituted material is a main component were obtained.

With respect to the Fr1, 450.3 which is M$^+$ of the tert-butyl-4-substituted benzofluoranthene as a main component was confirmed by MALDI-TOF MS (matrix-assisted desorption ionization-time of flight mass spectrometry). In contrast, when Fr2 was similarly analyzed, 506.4 which is M$^+$ of the tert-butyl-5-substituted benzofluoranthene as a main component was confirmed.

HPLC confirmed that the content of the tert-butyl-4-substituted material in the Fr1 was 73.2% and that the content of the tert-butyl group-5-substituted material in the Fr1 was 18.3%. In contrast, the content of the tert-butyl-4-substituted material in the Fr2 was 18.9% and the content of the tert-butyl-5-substituted material in the Fr2 was 66.4%.

EXAMPLE 2

Method of Producing Exemplified Compound No. 216

Exemplified Compound No. 216 of the present invention was manufactured by a method described below.

(1) Synthesis of Intermediate Compound 1 (5-chlorobenzo (ghi)fluranthene)

1-chloro-2-iodo-4-methoxybenzene was obtained using 2-chloro-5-methoxyaniline as a starting material by a method represented by Reaction Scheme (1). At this time, a synthesizing method described in Journal of Organic Chemistry 1983, 48, 4396 was referred to.

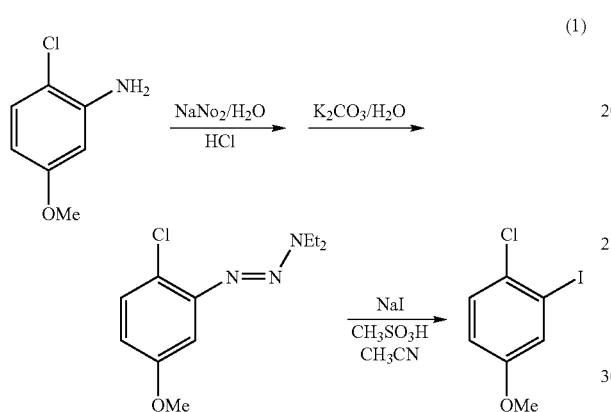

(1)

Next, 4-chloro-1-methoxybenzo(c)phenanthrene was obtained using 1-chloro-2-iodo-4-methoxybenzene as a starting material by a method represented by Reaction Scheme (2). At this time, a synthesizing method described in Journal of Organic Chemistry 1991, 56, 3769 was referred to.

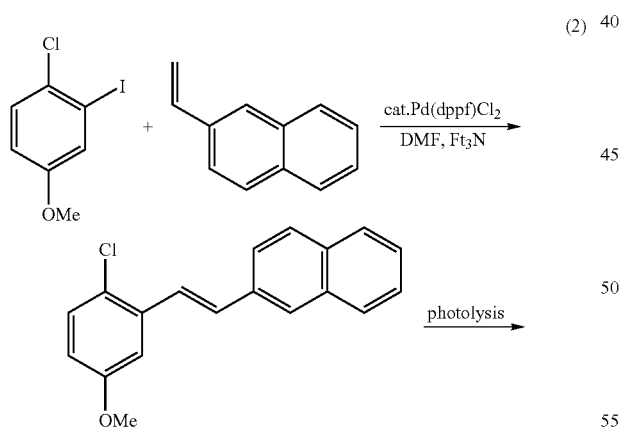

(2)

Next, intermediate compound 1 (5-chlorobenzo(ghi)fluranthene) was obtained using the 4-chloro-1-methoxybenzo (c)phenanthrene as the starting material by a method represented by Reaction Scheme (3). At this time, a synthesizing method described in Journal of Organic Chemistry 2000, 41, 285 was referred to.

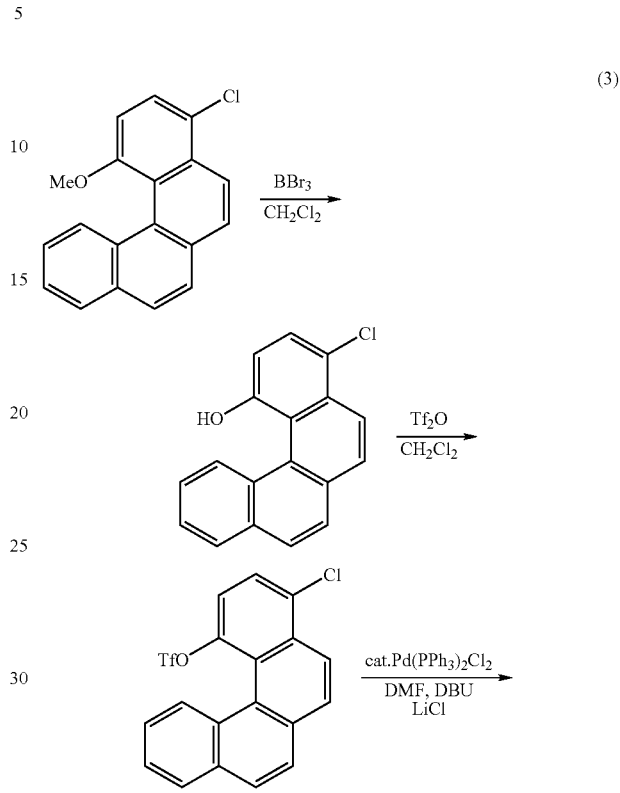

(3)

(2) Synthesis of Exemplified Compound No. 216

Exemplified Compound No. 216 was synthesized by a method represented by Reaction Scheme (4) using the intermediate compound 1 (5-chlorobenzo(ghi)fluranthene) obtained according to Reaction Scheme (3) above as a starting material. At this time, a synthesizing method described in Journal of American Chemical Society 2005, 127, 4685 was referred to.

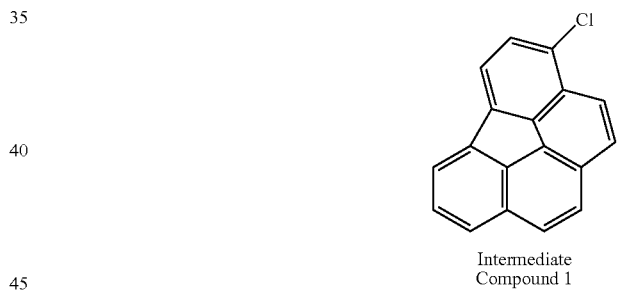

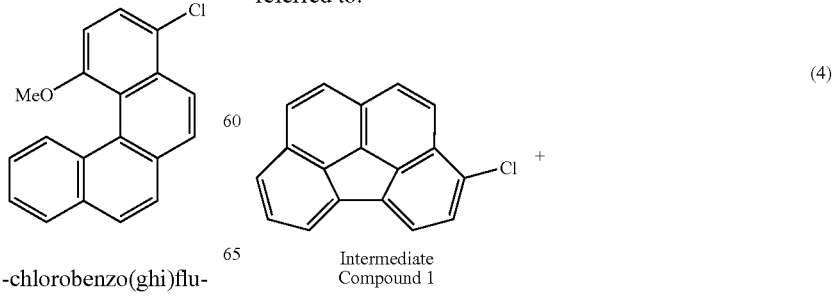

(4)

-continued

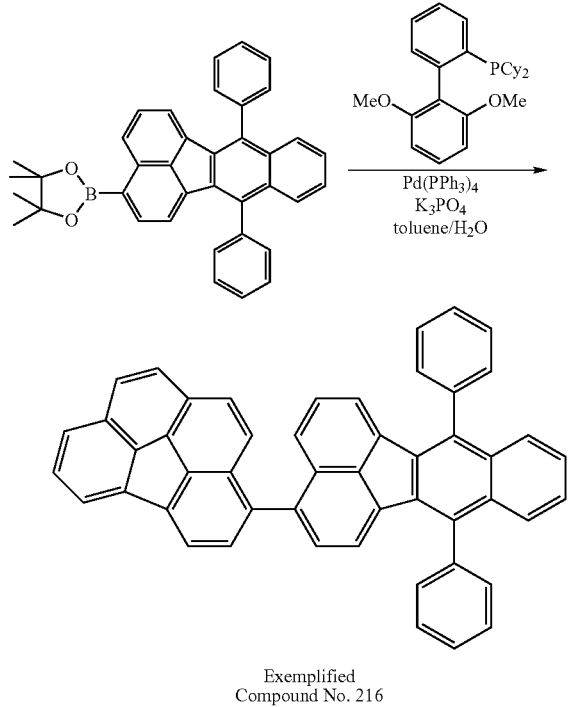

Exemplified Compound No. 216

Hereinafter, the details of the synthesis of Exemplified Compound No. 216 will be described.

The following reagents and a solvent were successively added to a 50 mL reactor in a stream of nitrogen.

5-chlorobenzo[ghi]fluoranthene: 112 mg (0.43 mmol)
2-(7,12-diphenylbenzo[k]fluoranthene-3-yl)-4,4,5,5-tetramethyl-1,3,2-dioxaborolan: 185 mg (0.345 mmol)
Dicyclohexyl(2',6'-dimethoxybiphenyl-2-yl)phosphin: 9.4 mg (0.024 mmol)
Tripotassium phosphate: 122 mg (0.57 mmol)
Toluene: 20 ml
Water: 2 ml
Palladium acetate: 2.6 mg (0.012 mmol)

Next, the reaction solution was stirred under reflux by heating for 12 hours, the resultant was cooled to room temperature, water was added, and then the stirring was stopped. Next, toluene was added, the organic layer was separated and washed twice with water, and then the solvent was distilled off under reduced pressure. The thus-obtained residue was purified by column chromatography (silica gel: 50 g, developing solvent: toluene/heptane=1/4). Next, by performing slurry washing using a mixed solvent of toluene and methanol, 110 mg of Exemplified Compound No. 216 was obtained as a pale yellow crystal.

The MALDI-TOF MS (matrix-assisted desorption ionization-time of flight mass spectrometry) confirmed 628.2 which is M⁺ of the compound.

$^1$H-NMR (CDCl$_3$): δ(ppm)=8.20 (d, 1H, J=7.32 Hz), 8.16 (d, 1H, J=6.86 Hz), 7.99 (d, 1H, J=8.69 Hz), 7.95 (d, 1H, J=8.23 Hz), 7.90 (d, 1H, J=8.69 Hz), 7.78 (d, 1H, J=8.69 Hz), 7.73-7.59 (m, 17H), 7.51 (d, 1H, J=7.32 Hz), 7.44-7.40 (m, 2H), 6.77 (d, 1H, J=7.32 Hz), 6.65 (d, 1H, J=6.86)

Figure 6:
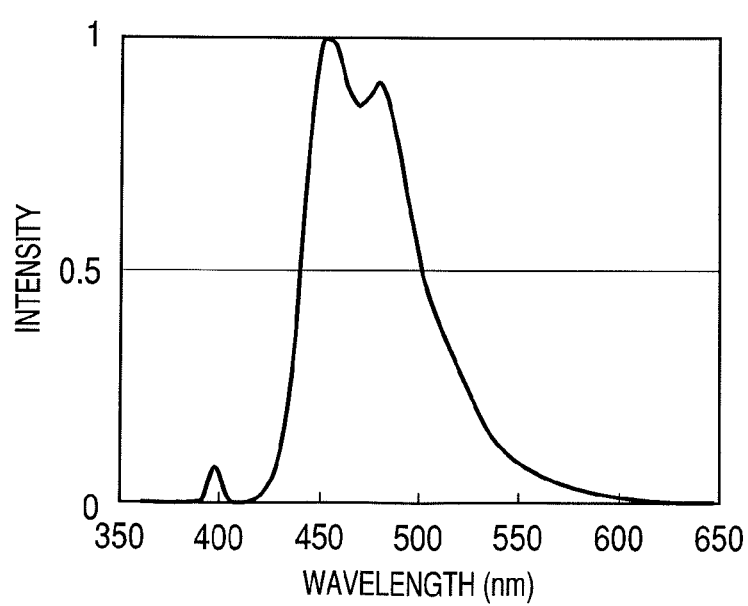
FIG. 6 is a view illustrating a PL spectrum of a toluene solution ($1.0 \times 10^{-5}$ mol/L) of Exemplified Compound No. 216.

Exemplified Compound No. 216 was measured for the light emitting (PL) spectrum of a toluene solution (1.0×10$^{-5}$ mol/L), and as a result, the spectrum illustrated in FIG. 6 was obtained. The spectrum revealed that the light emission peak of Exemplified Compound No. 216 was 456 nm, the half band width thereof was 67 nm, and blue light was emitted.

Next, the light emission quantum efficiency in the toluene solution of Exemplified Compound No. 216 was determined. More specifically, Exemplified Compound No. 216 was measured for the absorbance at 345 nm by preparing a toluene solution with a concentration of 10$^{-6}$ mol/l and using a spectrophotometer (U-3310, manufactured by Hitachi, Ltd.). Further, a light-emitting area when a wavelength of 345 nm was defined as an excitation wavelength was measured using a spectrophotofluorometer (F-4500, manufactured by Hitachi, Ltd.). A relative value of the light emission quantum efficiency when diphenylanthracene was adjusted to 0.95 was determined using the absorbance and the light-emitting area. The results are illustrated in Table 2.

Moreover, the following compounds are used in place of the 2-(7,12-diphenylbenzo(k)fluoranthene-3-yl)-4,4,5,5-tetramethyl-1,3,2-dioxaborolan which was used in the item (2) of this example. Exemplified Compounds shown below can be synthesized following the same procedure of Example 2 except the above.

(Exemplified Compound No. 134): 4,4,5,5-tetramethyl-2-(9,9,9',9'-tetramethyl-9H,9H'-2,2'-bifluorene-7-yl)-1,3,2-dioxaborolan (Exemplified Compound No. 201): 4,4,5,5-tetramethyl-2-(pyrene-1-yl)-1,3,2-dioxaborolan (Exemplified Compound No. 203): 2-(fluoranthene-3-yl)-4,4,5,5-tetramethyl-1,3,2-dioxaborolan (Exemplified Compound No. 205): 2-(chrysene-6-yl)-4,4,5,5-tetramethyl-1,3,2-dioxaborolan (Exemplified Compound No. 207): 2-(7-tert-butylpyrene-2-yl)-4,4,5,5-tetramethyl-1,3,2-dioxaborolan (Exemplified Compound No. 208): 2-(benzo[ghi]-fluoranthene-5-yl)-4,4,5,5-tetramethyl-1,3,2-dioxaborolan Comparative Example 1

The compound A-O represented by the following formulae were determined for the light emission quantum efficiency by the same procedure as in Example 2. The results are shown in Table 2.

TABLE 2

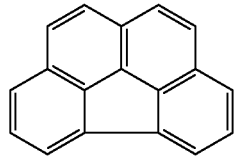

Compound A-0

| | Used compound | Relative quantum efficiency |
|---|---|---|
| Example 2 | Exemplified Compound No. 216 | 0.77 |
| Comparative Example 1 | Compound A-O | 0.20 |

EXAMPLE 3

Method of Producing Exemplified Compound No. 501

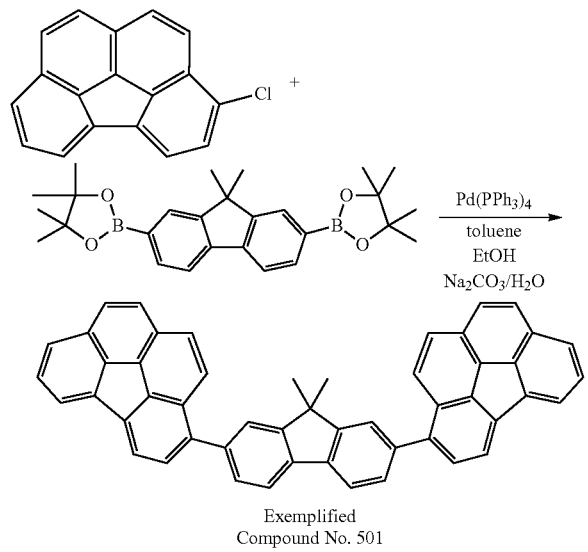

Exemplified Compound No. 501

The following reagents were suspended in a mixed solvent of 15 mL of toluene, 8 mL of ethanol, and 6 mL of 10% aqueous sodium carbonate solution in a 50 mL reactor in a stream of nitrogen.

5-chlorobenzo[ghi]fluoranthene: 300 mg (1.15 mmol)

2,2-(9,9'-dimethyl-9H-fluorene-2,7-diyl)-bis(4,4,5,5-tetramethyl-1,3,2-dioxaborolan): 257 mg (0.57 mmol)

Tetrakistriphenylphosphine palladium: 66 mg (0.06 mmol)

Next, the reaction solution was stirred under reflux by heating for 4 hours, the resultant was cooled to room temperature, and then water was added to thereby stop the reaction. Next, the organic layer was separated, and then washed twice with water. Then, the solvent was distilled off under reduced pressure. The thus-obtained residue was determined for the molecular weight by MALDI-TOF MS (matrix-assisted desorption ionization-time of flight mass spectrometry). As a result, 642.2 which is $M^+$ of Exemplified Compound No. 501 was confirmed.

In place of the 2,2-(9,9'-dimethyl-9H-fluorene-2,7-diyl)-bis(4,4,5,5-tetramethyl-1,3,2-dioxaborolan) of this example, the following compounds are used. The Exemplified Compounds shown below can be synthesized by the same method as in Example 3 except the above.

(Exemplified Compound No. 401): 1,4-biphenyl boronic acid (Exemplified Compound No. 407): biphenyl-4,4'-diyl boronic acid (Exemplified Compound No. 504): 2,7-bis(4,4,5,5-tetramethyl-1,3,2-dioxaborolan-2-yl)naphthalene (Exemplified Compound No. 506): 2,6-bis(4,4,5,5-tetramethyl-1,3,2-dioxaborolan-2-yl)naphthalene (Exemplified Compound No. 505): naphthalene-1,4-diboronic acid (Exemplified Compound No. 507): naphthalene-1,5-diboronic acid (Exemplified Compound No. 508): anthracene-9,10-diboronic acid (Exemplified Compound No. 510): chrysene-6,12-diboronic acid

EXAMPLE 4

An organic light emitting device having the structure illustrated in FIG. 2 was produced by a method described below.

As an anode 2, a film of tin oxide indium (ITO) having a thicknesses of 120 nm was formed on a glass substrate (substrate 1) by a sputtering method. Next, the glass substrate on which the ITO film was formed was subjected to ultrasonic cleaning with acetone and isopropyl alcohol (IPA) in this order. Then, the resultant was washed in boiling IPA, followed by drying. Further, the resultant was subjected to UV/ozone cleaning. The thus-treated glass substrate was used as a transparent conductive supporting substrate.

A 0.1 wt % chloroform solution using, as a solute, Compound A1 represented by the following formula was prepared as a material having positive hole transporting properties and a 0.1 wt % chloroform solution using, as a solute, the Fr1 in which a tert-butyl-4-substituted material is a main component, was prepared as a light emitting material. The solutions prepared were mixed at a (compound A1):(Fr1) volume ratio of 75:25.

Compound A1

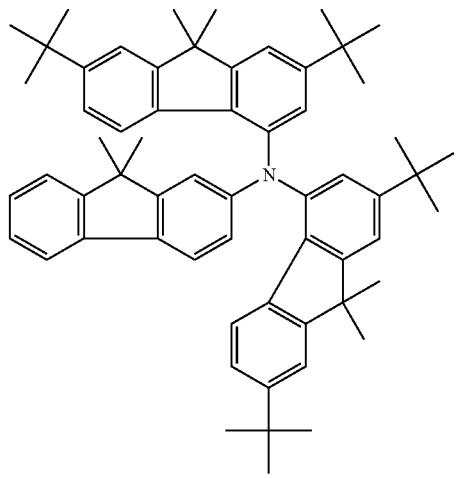

The resultant solution was added dropwise on the ITO electrode, and then spin coated at 500 RPM for 10 seconds, and then at 1000 RPM for 40 seconds to thereby form a film. Thereafter, the resultant was dried in a vacuum oven having a temperature of 80° C. for 10 minutes to thereby thoroughly remove the solvent in the thin film. Thus, a hole transporting layer 5 was formed.

Further, as an electron transporting layer 6, a film of 2,9-bis(2-(9,9'-dimethylfluorenyl))-1,10-phenanthroline having a film thicknesses of 25 nm was formed by a vacuum vapor deposition method. As deposition conditions, the degree of vacuum at the time of deposition was adjusted to $1.0 \times 10^{-4}$ Pa and the film formation rate was adjusted to 0.1 to 0.2 nm/sec.

Subsequently, a film of lithium fluoride (LiF) having a thicknesses of 0.5 nm as formed by a vacuum vapor deposition method on the organic layer. Further, an aluminum film having a film thicknesses of 100 nm was formed by a vacuum vapor deposition method to be used as an electron injecting electrode (cathode 4). As deposition conditions, the degree of vacuum at the time of deposition was adjusted to $1.0 \times 10^{-4}$ Pa, the film formation rate of the lithium fluoride film was adjusted to 0.05 nm/sec, and the film formation rate of aluminum was adjusted to 1.0 to 1.2 nm/sec.

Next, the organic light emitting device was covered with a protective glass plate in a dry air atmosphere so as not to be deteriorated by adsorption of moisture, and then sealed with an acrylic resin binder. The organic light emitting device was obtained as described above.

When a voltage of 6V was applied to the obtained organic light emitting device using the ITO electrode (anode 2) as an positive electrode and the Al electrode (cathode 4) as a negative electrode, the light emission of blue light of 300 cd/m² was observed.

EXAMPLE 5

The organic light emitting device having the structure illustrated in FIG. 4 was produced by a procedure described below.

As an anode 2, a film of tin oxide indium (ITO) having a thicknesses of 120 nm was formed on a glass substrate (substrate 1) by a sputtering method. Next, the glass substrate on which the ITO film was formed was subjected to ultrasonic cleaning with acetone and isopropyl alcohol (IPA) in this order. Then, the resultant was washed in boiling IPA, followed by drying. Further, the resultant was subjected to UV/ozone cleaning. The thus-treated glass substrate was used as a transparent conductive supporting substrate.

A 0.1 wt % chloroform solution using, as a solute, Compound A2 represented by the following formula was prepared as a hole injecting material.

Compound A2

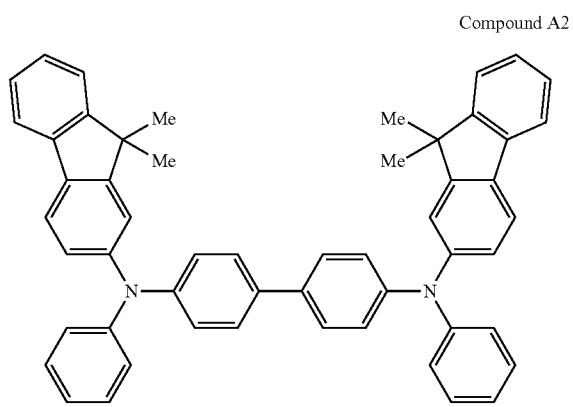

The resultant solution was added dropwise on the ITO electrode, and then spin coated at 500 RPM for 10 seconds, and then at 1000 RPM for 40 seconds to thereby form a film. Thereafter, the resultant was dried in a vacuum oven having a temperature of 80° C. for 10 minutes to thereby thoroughly remove the solvent in the thin film. Thus, a hole injecting layer 5 was formed.

Next, a film of Compound A1 represented by the following formula having a thicknesses of 15 nm was formed as a hole transporting layer 5 on the hole injecting layer 7 by a vacuum vapor deposition method.

Compound A1

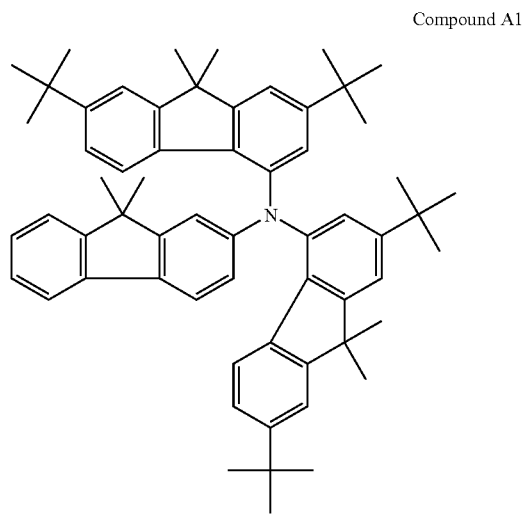

Vapor co-deposition of Exemplified Compound No. 216 and Compound A3 represented by the following formula was carried out in such a manner as to have a weight ratio of 2:98 to thereby form a light emitting layer 3. At this time, the film thickness of the light emitting layer 3 was 30 nm. The degree of vacuum at the time of deposition was adjusted to $1.0 \times 10^{-4}$ Pa and the film formation rate was adjusted to not less than 0.1 nm/sec and not more than 0.2 nm/sec.

Compound A3

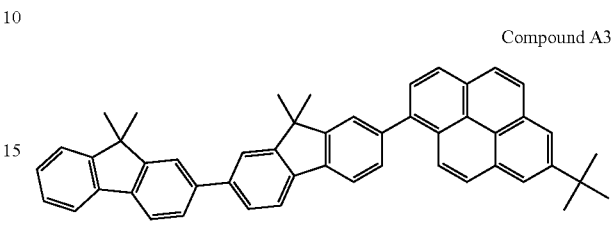

Further, as an electron transporting layer 6, a film of 2,9-bis(2-(9,9'-dimethylfluorenyl))-1,10-phenanthroline having a thicknesses of 30 nm was formed by a vacuum vapor deposition method. As deposition conditions, the degree of vacuum at the time of deposition was adjusted to $1.0 \times 10^{-4}$ Pa and the film formation rate was adjusted to 0.1 nm/sec or more to 0.2 nm/sec or less.

Next, a film of lithium fluoride (LiF) having a thicknesses of 0.5 nm was formed by a vacuum vapor deposition method on the electron transporting layer 6. At this time, the degree of vacuum at the time of deposition was adjusted to $1.0 \times 10^{-4}$ Pa and the film formation rate was adjusted to 0.01 nm/sec. Next, a 100 nm thick aluminum film was formed by a vacuum vapor deposition method. At this time, the degree of vacuum at the time of deposition was adjusted to $1.0 \times 10^{-4}$ Pa and the film formation rate was adjusted to 0.5 nm/sec or more to 1.0 nm/sec or less. Here, the lithium fluoride film and the aluminum film function as an electron injecting electrode (cathode 4).

Next, the organic light emitting device was covered with a protective glass plate in a dry air atmosphere so as not to be deteriorated by adsorption of moisture, and then sealed with an acrylic resin binder.

The organic light emitting device was obtained as described above.

A voltage of 4.3V was applied to the obtained device using the ITO electrode (anode 2) as a positive electrode and the Al electrode (cathode 4) as a negative electrode. As a result, the light emission of blue light having a light emitting efficiency of 6.0 cd/A was observed. Moreover, with respect to the CIE chromaticity, the light emission of blue light in which x was 0.15 and y was 0.20 was observed.

Further, a voltage was applied to the device for 100 hours while maintaining the current density of 100 mA/cm² under a nitrogen atmosphere. As a result, the luminance after 100 hours have passed was 4557 cd/m² relative to the initial luminance of 5239 cd/m², which showed that the deterioration in the luminance was low.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-127794, filed May 14, 2007, which is hereby incorporated by reference herein in its entirety.

What is claimed is:

1. A benzo(ghi)fluoranthene derivative represented by General Formula (1):

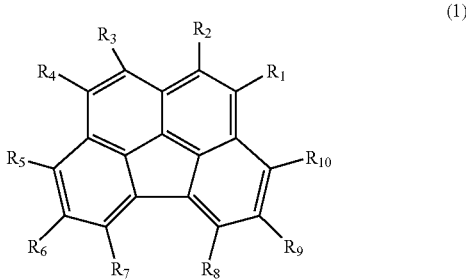

wherein $R_1$ to $R_4$ and $R_6$ to $R_9$ each represent a hydrogen atom; and $R_5$ represents benzo[k]fluoranthene, wherein the benzo[k]fluoranthene are optionally substituted with a phenyl group or an alkyl group, and the phenyl group is optionally substituted with an alkyl group.

2. A benzo(ghi)fluoranthene derivative represented by the following formula:

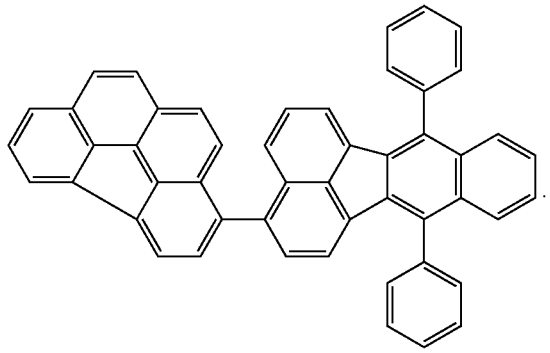

3. An organic light emitting device comprising a pair of electrodes and a light emitting layer sandwiched between the pair or electrodes, wherein the light emitting layer comprises the benzo(ghi)fluoranthene derivative according to claim 2.

4. An organic light emitting device comprising a pair of electrodes and a light emitting layer sandwiched between the pair or electrodes, wherein the light emitting layer comprises the benzo(ghi)fluoranthene derivative according to claim 1.

5. The organic light emitting device according to claim 3, wherein the light emitting layer comprises a host material and a guest material, and the host material is represented by the following formula:

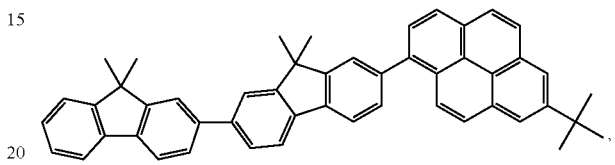

and the guest material is represented by the following formula:

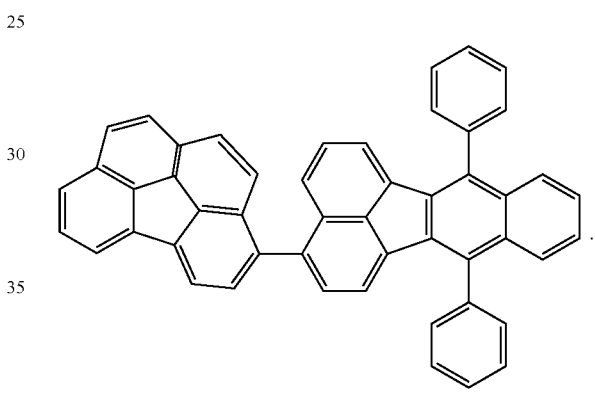

* * * * *